US011613524B2

(12) United States Patent
Schaub et al.

(10) Patent No.: US 11,613,524 B2
(45) Date of Patent: Mar. 28, 2023

(54) MONOMERS COMPRISING AT LEAST ONE 4-(2-OXYETHYLIDENE)-1,3-DIOXOLAN-2-ONE UNIT AND USE THEREOF

(71) Applicant: BASF SE, Ludwigshafen am Rhein (DE)

(72) Inventors: Thomas Schaub, Ludwigshafen (DE); Peter Rudolf, Ludwigshafen (DE); Ulrike Licht, Ludwigshafen (DE); Verena Mormul, Ludwigshafen (DE); Saumya Dabral, Heidelberg (DE)

(73) Assignee: BASF SE, Ludwigshafen am Rhein (DE)

( * ) Notice: Subject to any disclaimer, the term of this patent is extended or adjusted under 35 U.S.C. 154(b) by 44 days.

(21) Appl. No.: 16/951,207

(22) Filed: Nov. 18, 2020

(65) Prior Publication Data
US 2021/0070728 A1     Mar. 11, 2021

Related U.S. Application Data

(63) Continuation-in-part of application No. PCT/EP2019/061774, filed on May 8, 2019.

(30) Foreign Application Priority Data

May 18, 2018  (EP) .................................... 18173232

(51) Int. Cl.
C07D 317/36    (2006.01)
C08F 136/20    (2006.01)
C09J 4/00      (2006.01)

(52) U.S. Cl.
CPC .......... *C07D 317/36* (2013.01); *C08F 136/20* (2013.01); *C09J 4/00* (2013.01)

(58) Field of Classification Search
CPC ......... C07D 317/36; C09J 4/00; C08F 136/20
See application file for complete search history.

(56) References Cited

U.S. PATENT DOCUMENTS

| 3,153,002 | A  | 10/1964 | Wismer et al.   |
| 4,247,654 | A  | 1/1981  | Wagner          |
| 5,990,245 | A  | 11/1999 | Esselborn et al.|
| 6,639,114 | B2 | 10/2003 | Ahlers et al.   |
| 8,118,968 | B2 | 2/2012  | Moeller et al.  |
| 8,197,944 | B2 | 6/2012  | Beck et al.     |
| 2013/0035432 | A1 | 2/2013 | Breu et al.    |
| 2016/0215162 | A1 | 7/2016 | Clauss et al.  |
| 2018/0155479 | A1 | 6/2018 | Litch et al.   |
| 2019/0241538 | A1 | 8/2019 | Litch et al.   |
| 2020/0339846 | A1 | 10/2020 | Schumacher    |

FOREIGN PATENT DOCUMENTS

| DE | 1064938 B        | 9/1959  |
| DE | 1176358 B        | 8/1964  |
| DE | 2639083 A1       | 3/1978  |
| DE | 2737951 A1       | 3/1979  |
| EP | 0622378 A1       | 11/1994 |
| EP | 3668849 A1       | 6/2020  |
| WO | WO-2006/010408 A1 | 2/2006 |
| WO | WO-2008/110394 A1 | 9/2008 |
| WO | WO-2011/089089 A1 | 7/2011 |
| WO | WO-2011/157671 A1 | 12/2011 |
| WO | WO-2012/175427 A2 | 12/2012 |
| WO | WO-2012/175431 A2 | 12/2012 |
| WO | WO-2013144299 A1 * | 10/2013 | ........... C07D 317/38 |

(Continued)

OTHER PUBLICATIONS

Barrett, et al.,"Rapid Entry into Mono-, Bi-, and Tricyclic β-Lactam Arrays via Alkene Metathesis", The Journal of Organic Chemistry, vol. 63, Issue 22, Oct. 1998, pp. 7893-7907.
Braverman, et al.,"Synthesis and structure of novel sulfur bridged cyclic di- and tetraalkynes", Tetrahedron Letters, vol. 42, Issue 42, Oct. 15, 2001, pp. 7485-7488.
Buzas, et al.,"Gold-catalyzed rearrangement of propargylic tert-butyl carbonates", Tetrahedron, vol. 65, Issue 9, Feb. 28, 2009, pp. 1889-1901.
De Frémont, et al., "Carbenes: Synthesis, properties, and organometallic chemistry", Coordination Chemistry Reviews, vol. 253, Issues 7-8, Apr. 2009, pp. 862-892.
European Search Report for EP Patent Application No. 18173232.2, dated Oct. 24, 2018, 4 pages.
International Search Report for PCT Patent Application No. PCT/EP2019/061774, dated Aug. 16, 2019, 5 pages.

(Continued)

*Primary Examiner* — Robert D Harlan
(74) *Attorney, Agent, or Firm* — Grüneberg and Myers, PLLC

(57) ABSTRACT

A compound of formula (I)

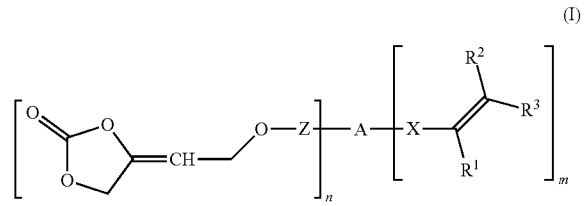

(I)

wherein $R^1$ is hydrogen or an organic radical of 1 to 100 carbon atoms, $R^2$, $R^3$ are independently hydrogen or an organic radical of 1 to 100 carbons, Z is a single bond or a divalent organic group of 1 to 100 carbons, A is an (n+m)-valent organic group of 1 to 1 000 000 carbons, X is a single bond or a divalent organic group of 1 to 40 carbons, n is an integer from 1 to 1000, m is 0, 1, or 2, the sum of n+m being an integer from 2 to 1002. Such compounds are obtainable from specific 4-oxy-but-2-yn-1-ol derivatives, or used as intermediate(s), crosslinker(s), or monomer(s) in polymerization or oligomerization reactions, or for two-component compositions having such compound(s) and multifunctional hardener(s). Such compound(s) may be used to prepare polyunsaturated compounds, by reaction with an (oligo/poly)-functional nucleophile, or polymers.

19 Claims, No Drawings

(56) References Cited

FOREIGN PATENT DOCUMENTS

| WO | WO-2015/039807 A1 | 3/2015 |
| WO | WO-2015/164692 A1 | 10/2015 |
| WO | WO-2016/202652 A1 | 12/2016 |
| WO | WO-2017/207461 A1 | 12/2017 |
| WO | WO-2018/054609 A1 | 3/2018 |
| WO | WO-2018/054713 A1 | 3/2018 |
| WO | WO-2019/034648 A1 | 2/2019 |

OTHER PUBLICATIONS

Karabiyikoglu, et al., "Cycloaddition Reactions of Cobalt-Complexed Macrocyclic Alkynes: The Transannular Pauson-Khand Reaction", The Journal of Organic Chemisrty, vol. 82, Issue 15, Jul. 2017, pp. 7732-7744.
Motoda, et al.,"PhosphaneFree Rhodium Catalyst in an Anionic Micellar System for [4+2] Annulation of Dienynes", Angewandte Chemie, vol. 43, Issue 14, Mar. 24, 2004, pp. 1860-1862.
Ruter, et al., "Polyester", Ullmanns Enzyklopädie der Technischen Chemie, 4th Edition, vol. 19, pp. 61-65.

* cited by examiner

MONOMERS COMPRISING AT LEAST ONE 4-(2-OXYETHYLIDENE)-1,3-DIOXOLAN-2-ONE UNIT AND USE THEREOF

CROSS-REFERENCE TO RELATED APPLICATIONS

The present application is a U.S. bypass continuation of International Application No. PCT/EP2019/061774, filed on May 8, 2019, published as WO 2019/219469 A1 on Nov. 21, 2019, and claims benefit to European Application No. 18 173 232.2, filed on May 18, 2018, each of which is incorporated herein by reference.

FIELD OF THE INVENTION

The present invention relates to a compound of formula (I)

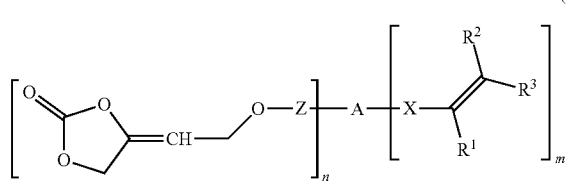

wherein $R^1$ is hydrogen or an organic radical having from 1 to 100 carbon atoms, $R^2$, $R^3$ independently of one another are hydrogen or an organic radical having from 1 to 100 carbon atoms, Z is a chemical single bond or a divalent organic group having from 1 to 100 carbon atoms, A is a (n+m)-valent organic group having from 1 to 1 000 000 carbon atoms, X is a chemical single bond or a divalent organic group having from 1 to 40 carbon atoms, n is an integer from 1 to 1000, m is 0, 1 or 2, wherein the sum of n+m is an integer from 2 to 1002.

The present invention further relates to processes for preparing compounds of formula (I), to specific 4-oxy-but-2-yn-1-ol derivatives as starting materials for the preparation of compounds of formula (I), to the use of the compound of formula (I) as intermediate or crosslinker or as monomer in polymerization reactions or in oligomerization reactions, to two-component compositions comprising as a first component at least one compound of formula (I), as a second component at least one multifunctional hardener, to polymers formed from one or more monomers, wherein at least one monomer is a compound of formula (I) and to the use of any compound described before as an intermediate for the preparation of polyunsaturated compounds by reacting a (oligo/poly)-functional nucleophile with a compound of formula (I). The reaction product can be subsequently applied to further curing (e.g. radical induced curing).

BACKGROUND OF THE INVENTION

Exo vinylene carbonates are valuable compounds, especially for the use as monomers in polymer applications as described in WO 2015/164692 A1, WO 2013/144299 A1, WO 2015/039807 and WO 2011/157671 A1.

For polymer applications on a larger scale, it is desirable to produce exo vinylene carbonates based on starting materials which are cheap and easily available. The most atom-efficient access to exo vinylene carbonates is via the carboxylation of 4-oxy-but-2-yn-1-ol derivatives with $CO_2$.

The 4-oxy-but-2-yn-1-ol derivative, which is industrially produced on the largest scale, is 1,4-butynediol. Therefore, this 4-oxy-but-2-yn-1-ol derivative is also the most available and cheapest 4-oxy-but-2-yn-1-ol derivative. Therefore, it is highly attractive to use 4-oxy-but-2-yn-1-ol derivatives, which are based on the readily available 1,4-butynediol, as starting materials for the production of exo vinylene carbonates, which can be used in polymer applications.

The exo vinylene carbonates with substituents in the 4,4-position are available via the reaction of secondary or tertiary propargylic alcohols with $CO_2$ using different catalysts like metals or bases.

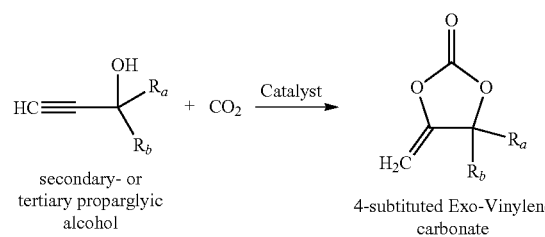

secondary- or tertiary propargylic alcohol 4-subtituted Exo-Vinylene carbonate

None of the protocols, which are described in the literature, like the Silver-, Copper-, Cobalt- or guanidine catalyzed cyclisation could until now be applied to the conversion of simple primary propargylic alcohols with $CO_2$ towards the simple Exo-vinylene carbonates with two hydrogens in the 4,4-positions.

Accordingly, an aspect of the invention provides new compounds comprising at least one 4-(2-oxyethylidene)-1, 3-dioxolan-2-one, which can be used as monomers in polymer applications and which are based on easily accessible 4-oxy-but-2-yn-1-ol derivatives, preferably based on 1,4-butynediol. Another aspect of the invention provides economic processes for producing said compounds, which can be used as intermediates, as crosslinkers or as monomers in polymer applications, wherein the starting materials are based on easily accessible 4-oxy-but-2-yn-1-ol derivatives, preferably based on 1,4-butynediol.

BRIEF SUMMARY OF THE INVENTION

One or more problems described above may be addressed by a compound of formula (I)

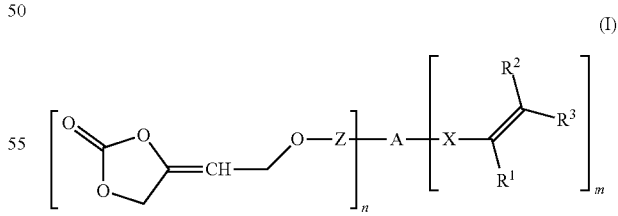

wherein
$R^1$ is hydrogen or an organic radical having from 1 to 100, preferably 1 to 40 carbon atoms, preferably hydrogen, $C_1$-$C_4$ alkyl, $CH_2COOR^4$, phenyl or phenyl-$C_1$-$C_4$ alkyl;
$R^2$, $R^3$ independently of one another are hydrogen or an organic radical having from 1 to 100, preferably 1 to 40 carbon atoms, preferably hydrogen or $C_1$-$C_4$ alkyl or one of the radicals, $R^2$ or $R^3$, may be $COOR^4$ or $CH_2COOR^4$, $R^4$ where present is hydrogen or an organic radical having from 1 to 100, preferably 1 to 40 carbon atoms, preferably hydrogen or $C_1$-$C_6$, Z is a chemical single bond or a divalent organic group having from 1 to 100, preferably 1 to 40 carbon atoms, A is a (n+m)-valent organic group having from 1 to 1 000 000 carbon atoms, X is a chemical single bond or a divalent organic group having from 1 to 40 carbon atoms, n is an integer from 1 to 1000, m is 0, 1 or 2, wherein the sum of n+m is an integer from 2 to 1002.

DETAILED DESCRIPTION OF THE INVENTION

The substituents according to the present invention are, unless restricted further, defined as follows:

The term "organic radical having from 1 to 100 carbon atoms" or "organic radical having from 1 to 40 carbon atoms" as used in the present text refers to, for example, $C_1$-$C_{40}$-alkyl radicals, $C_1$-$C_{10}$-fluoroalkyl radicals, $C_1$-$C_{12}$-alkoxy radicals, saturated $C_3$-$C_{20}$-heterocyclic radicals, $C_6$-$C_{40}$-aryl radicals, $C_2$-$C_{40}$-heteroaromatic radicals, $C_6$-$C_{10}$-fluoroaryl radicals, $C_6$-$C_{10}$-aryloxy radicals, silyl radicals having from 3 to 24 carbon atoms, $C_2$-$C_{20}$-alkenyl radicals, $C_2$-$C_{20}$-alkynyl radicals, $C_7$-$C_{40}$-arylalkyl radicals or $C_8$-$C_{40}$-arylalkenyl radicals. An organic radical is in each case derived from an organic compound. Thus, the organic compound methanol can in principle give rise to three different organic radicals having one carbon atom, namely methyl ($H_3C$—), methoxy ($H_3C$—O—) and hydroxymethyl ($HOC(H_2)$—). Therefore, the term "organic radical having from 1 to 100 carbon atoms" comprises beside alkoxy radicals for example also dialkylamino radicals, monoalkylamino radicals or alkylthio radicals.

In the present description, the term radical is used interchangeably with the term group, when defining the variables $R^x$ in the presented formulas.

The term "alkyl" as used in the present text encompasses linear or singly or multiply branched saturated hydrocarbons which can also be cyclic. Preference is given to a $C_1$-$C_{18}$-alkyl radical such as methyl, ethyl, n-propyl, n-butyl, n-pentyl, n-hexyl, n-heptyl, n-octyl, n-nonyl, n-decyl, cyclopentyl, cyclohexyl, isopropyl, isobutyl, isopentyl, isohexyl, sec-butyl or tert-butyl.

The term "alkenyl" as used in the present text encompasses linear or singly or multiply branched hydrocarbons having one or more C—C double bonds which can be cumulated or alternating.

The term "saturated heterocyclic radical" as used in the present text refers to, for example, monocyclic or polycyclic, substituted or unsubstituted aliphatic or partially unsaturated hydrocarbon radicals in which one or more carbon atoms, CH groups and/or $CH_2$ groups have been replaced by heteroatoms which are preferably selected from the group consisting of the elements O, S, N and P. Preferred examples of substituted or unsubstituted saturated heterocyclic radicals are pyrrolidinyl, imidazolidinyl, pyrazolidinyl, piperidyl, piperazinyl, morpholinyl, tetrahydrofuranyl, tetrahydropyranyl, tetrahydrothiophenyl and the like, and also methyl-, ethyl-, propyl-, isopropyl- and tert-butyl-substituted derivatives thereof.

The term "aryl" as used in the present text refers to, for example, aromatic and optionally fused polyaromatic hydrocarbon radicals which may be monosubstituted or polysubstituted by linear or branched $C_1$-$C_{18}$-alkyl, $C_1$-$C_{18}$-alkoxy, $C_2$-$C_{10}$-alkenyl or halogen, in particular fluorine. Preferred examples of substituted and unsubstituted aryl radicals are, in particular, phenyl, pentafluorophenyl, 4-methylphenyl, 4-ethylphenyl, 4-n-propylphenyl, 4-isopropylphenyl, 4-tert-butylphenyl, 4-methoxyphenyl, 1-naphthyl, 9-anthryl, 9-phenanthryl, 3,5-dimethylphenyl, 3,5-di-tert-butylphenyl or 4-trifluoromethylphenyl.

The term "heteroaromatic radical" as used in the present text refers to, for example, aromatic hydrocarbon radicals in which one or more carbon atoms or CH groups have been replaced by nitrogen, phosphorus, oxygen or sulfur atoms or combinations thereof. These may, like the aryl radicals, optionally be monosubstituted or polysubstituted by linear or branched $C_1$-$C_{18}$-alkyl, $C_2$-$C_{10}$-alkenyl or halogen, in particular fluorine. Preferred examples are furyl, thienyl, pyrrolyl, pyridyl, pyrazolyl, imidazolyl, oxazolyl, thiazolyl, pyrimidinyl, pyrazinyl and the like, and also methyl-, ethyl-, propyl-, isopropyl- and tert-butyl-substituted derivatives thereof.

The term "arylalkyl" as used in the present text refers to, for example, aryl-comprising substituents whose aryl radical is linked via an alkyl chain to the remainder of the molecule. Preferred examples are benzyl, substituted benzyl, phenethyl, substituted phenethyl and the like.

The terms fluoroalkyl and fluoroaryl mean that at least one hydrogen atom, preferably more than one and at most all hydrogen atoms, of the corresponding radical have been replaced by fluorine atoms. Examples of preferred fluorine-comprising radicals are trifluoromethyl, 2,2,2-trifluoroethyl, pentafluorophenyl, 4-trifluoromethylphenyl, 4-perfluoro-tert-butylphenyl and the like.

With regard to preferred embodiments of the invention, the radicals, groups or variables $R^1$, $R^2$, $R^3$, $R^4$, Z, A, n and m in the compounds of the formula (I) preferably each independently have one or more or all of the following definitions:

$R^1$ is hydrogen or an organic radical having from 1 to 100, preferably 1 to 40 carbon atoms. Preferably $R^1$ is hydrogen, $C_1$-$C_4$ alkyl, such as methyl, ethyl, n-propyl, i-propyl, n-butyl, i-butyl or sec.-butyl, or $R^1$ is $CH_2COOR^4$, phenyl or phenyl-$C_1$-$C_4$ alkyl. Particularly preferably $R^1$ is hydrogen or methyl.

$R^2$ is hydrogen or an organic radical having from 1 to 100, preferably 1 to 40 carbon atoms. Preferably $R^2$ is hydrogen, $C_1$-$C_4$ alkyl, such as methyl, ethyl, n-propyl, i-propyl, n-butyl, i-butyl or sec.-butyl, or $R^2$ is $COOR^4$ or $CH_2COOR^4$. Particularly preferably $R^2$ is hydrogen.

$R^3$ is hydrogen or an organic radical having from 1 to 100, preferably 1 to 40 carbon atoms. Preferably $R^3$ is hydrogen, $C_1$-$C_4$ alkyl, such as methyl, ethyl, n-propyl, i-propyl, n-butyl, i-butyl or sec.-butyl, or $R^3$ is $COOR^4$ or $CH_2COOR^4$. Particularly preferably $R^3$ is hydrogen.

$R^4$, if present, is hydrogen or an organic radical having from 1 to 100, preferably 1 to 40 carbon atoms. Preferably $R^4$ is hydrogen or $C_1$-$C_6$ alkyl, such as methyl, ethyl, n-propyl, i-propyl, n-butyl, i-butyl, sec.-butyl, n-pentyl, n-hexyl or cyclohexyl. Particularly preferably $R^4$ is $C_1$-$C_4$ alkyl.

Z is a chemical single bond or a divalent organic group having from 1 to 100, preferably 1 to 40 carbon atoms. Preferably Z is a chemical single bond or a divalent organic group selected from the group of elements consisting of —$CH_2$—, —$PO_2$—, —$SO_2$—, —C(=O)—, —C(=O)—O— and —C(=O)—N($R^5$)—, where $R^5$ is hydrogen, $C_1$-$C_4$ alkyl or phenyl, preferably hydrogen.

A is a (n+m)-valent organic group having from 1 to 1 000 000 carbon atoms. Preferably the (n+m)-valent organic group A is derived from an organic compound selected from the group consisting of $C_1$-$C_{40}$-alkanes, $C_1$-$C_{40}$-alkenes, saturated $C_3$-$C_{100}$-heterocycles, aromatic $C_6$-$C_{40}$-hydrocarbons, $C_2$-$C_{40}$-heteroarenes, $C_7$-$C_{40}$-arylalkanes and $C_8$-$C_{40}$-arylalkenes, wherein in each member of the group, one or more hydrogen atoms can be substituted by halogens, OH, $-NR^6_2$ or $-CN$ and one or more $CH_2$-groups can be substituted by $-O-$, $-S-$, $-N(R^6)-$, $PO_2-$, $-SO_2-$, $-C(=O)-$, $-C(=O)-O-$ or $-C(=O)-N(R^5)-$, wherein $R^6$ is hydrogen, $C_1$-$C_4$ alkyl or phenyl, and from polymers, which are selected from the group of polymers consisting of poly(meth) acrylates, polyesters, polyurethanes, polyethers, polyamides, polycarbonates and polyolefins.

X is a chemical single bond or a divalent organic group having from 1 to 40 carbon atoms. Preferably X is a chemical single bond or a divalent organic group selected from the group of elements consisting of $-C(=O)-$, $-O-C(=O)-$ and $-N(R^5)-C(=O)-$, where $R^5$ is hydrogen, $C_1$-$C_4$ alkyl or phenyl, preferably hydrogen.

The variable n is an integer from 1 to 1000. Preferably n is 1, 2, 3, 4, 5 or 6, more preferably 2, 3 or 4, even more preferably 2 or 3, in particular 2.

The variable m is 0, 1 or 2, preferably 0 or 1, in particular 0.

The sum of n+m is an integer from 2 to 1002. Preferably the sum of n+m is 2, 3, 4, 5 or 6, more preferably 2 or 3, in particular 2.

In cases wherein the variable n is 2 or more, the two or more Z groups can be all identical or can be independently from each other different. Preferably, two or more Z groups are identical, disregarding different isotopes of a chemical element in an organic group. In the context of the present invention, the organic groups $-^{12}C(=O)-$ and $-^{13}C(=O)-$ are considered to be identical.

In cases wherein m is two, the two X groups can be also identical or different.

An inventive compound of formula (I) may be characterized in that
$R^1$ is hydrogen, $C_1$-$C_4$ alkyl, $CH_2COOR^4$, phenyl or phenyl-$C_1$-$C_4$ alkyl;
$R^2$, $R^3$ independently of one another are hydrogen or $C_1$-$C_4$ alkyl or one of the radicals, $R^2$ or $R^3$, may be $COOR^4$ or $CH_2COOR^4$,
$R^4$ where present is hydrogen or $C_1$-$C_6$ alkyl.

An inventive compound of formula (I) may be characterized in that
Z is a chemical single bond or a divalent organic group selected from the group of elements consisting of $-CH_2-$, $-PO_2-$, $-SO_2-$, $-C(=O)-$, $-C(=O)-O-$ and $-C(=O)-N(R^5)-$, where $R^5$ is hydrogen, $C_1$-$C_4$ alkyl or phenyl, preferably hydrogen.

An inventive compound of formula (I) may be characterized in that
X is chemical single bond or a divalent organic group selected from the group of elements consisting of $-C(=O)-$, $-O-C(=O)-$ and $-N(R^5)-C(=O)-$, where $R^5$ is hydrogen, $C_1$-$C_4$ alkyl or phenyl, preferably hydrogen.

An inventive compound of formula (I) may be characterized in that
n is 1, 2, 3, 4, 5 or 6, preferably 2, 3 or 4, more preferably 2 or 3, in particular 2,
m is 0, 1 or 2, preferably 0 or 1, in particular 0,
wherein the sum of n+m is 2, 3, 4, 5 or 6, preferably 2 or 3, in particular 2.

An inventive compound of formula (I) may be characterized in that the (n+m)-valent organic group A is derived from an organic compound selected from the group consisting of $C_1$-$C_{40}$-alkanes, $C_1$-$C_{40}$-alkenes, saturated $C_3$-$C_{100}$-heterocycles, aromatic $C_6$-$C_{40}$-hydrocarbons, $C_2$-$C_{40}$-heteroarenes, $C_7$-$C_{40}$-arylalkanes and $C_8$-$C_{40}$-arylalkenes, wherein in each member of the group, one or more hydrogen atoms can be substituted by halogens, $-NR^6_2$, CN or OH and one or more $CH_2$-groups can be substituted by $-O-$, $-S-$, $-N(R^6)-$, $PO_2-$, $-SO_2-$, $-C(=O)-$, $-C(=O)-O-$ or $-C(=O)-N(R^5)-$, wherein $R^5$ is hydrogen, $C_1$-$C_4$ alkyl or phenyl, preferably hydrogen and wherein $R^6$ is hydrogen, $C_1$-$C_4$ alkyl or phenyl, and from polymers, which are selected from the group of polymers consisting of poly(meth) acrylates, polyesters, polyurethanes, polyethers, polyhydroxy ethers, polyamides, polycarbonates and polyolefins.

An inventive compound of formula (I) may be characterized in that
$R^1$ is hydrogen, $C_1$-$C_4$ alkyl, $CH_2COOR^4$, phenyl or phenyl-$C_1$-$C_4$ alkyl, preferably $R^1$ is hydrogen or methyl,
$R^2$, $R^3$ independently of one another are hydrogen or $C_1$-$C_4$ alkyl or one of the radicals, $R^2$ or $R^3$, may be $COOR^4$ or $CH_2COOR^4$, preferably $R^2$, $R^3$ are both hydrogen,
$R^4$ where present is hydrogen or $C_1$-$C_6$ alkyl, preferably $R^4$ is $C_1$-$C_4$ alkyl,
Z is a chemical single bond or a divalent organic group selected from the group of elements consisting of $-CH_2-$, $-PO_2-$, $-SO_2-$, $-C(=O)-$, $-C(=O)-O-$ and $-C(=O)-N(R^5)-$,
A is a divalent organic group derived from an organic compound selected from the group consisting of $C_1$-$C_{40}$-alkanes, $C_1$-$C_{40}$-alkenes, saturated $C_3$-$C_{20}$-heterocycles, aromatic $C_6$-$C_{40}$-hydrocarbons, $C_2$-$C_{40}$-heteroarenes, $C_7$-$C_{40}$-arylalkanes and $C_8$-$C_{40}$-arylalkenes, wherein in each member of the group, one or more hydrogen atoms can be substituted by halogens, OH, $-NR^6_2$ or $-CN$, and one or more $CH_2$-groups can be substituted by $-O-$, $-S-$, $-N(R^6)-$, $PO_2-$, $-SO_2-$, $-C(=O)-$, $-C(=O)-O-$ or $-C(=O)-N(R^5)-$,
X is chemical single bond or a divalent organic group selected from the group of elements consisting of $-C(=O)-$, $-O-C(=O)-$ and $-N(R^5)-C(=O)-$, wherein $R^5$ is hydrogen, $C_1$-$C_4$ alkyl or phenyl, preferably hydrogen, and wherein $R^6$ is hydrogen, $C_1$-$C_4$ alkyl or phenyl,
n is 1,
m is 1.

Compounds of formula (I), wherein m is 0 and n is 2, 3, 4, 5 or 6, preferably 2, 3 or 4, more preferably 2 or 3, in particular 2, are also valuable monomers in polymerization reactions or as intermediate in the reaction with nucleophiles, in particular, as monomers for the formation of poly(keto urethanes), poly(keto carbonates), poly(keto thiocarbonates), poly(keto ethers) or polymers comprising a mixture of the functional groups selected from the group consisting of keto urethanes, keto carbonates, keto thiocarbonates and keto ethers.

Compounds of formula (I), wherein m is 1 or 2, preferably 1, and n=1 are also valuable as monomer for the formation of polyunsaturated urethanes, polyunsaturated carbonates, polyunsaturated thiocarbonates, or polymers comprising a mixture of the functional groups selected from the group consisting of unsaturated urethanes, unsaturated carbonates, unsaturated thiocarbonates.

An inventive compound of formula (I) may be characterized in that n is 2, 3, 4, 5 or 6, preferably 2, 3 or 4, more preferably 2 or 3, in particular 2, m is 0, Z is a chemical single bond or a divalent organic group selected from the group of elements consisting of —$CH_2$—, —$PO_2$—, —$SO_2$—, —$C(=O)$—, —$C(=O)$—O— and —$C(=O)$—$N(R^5)$—, A is a n-valent organic group, which is derived from an organic compound selected from the group consisting of $C_1$-$C_{40}$-alkanes, $C_1$-$C_{40}$-alkenes, saturated $C_3$-$C_{100}$-heterocycles, aromatic $C_6$-$C_{40}$-hydrocarbons, $C_2$-$C_{40}$-heteroarenes, $C_7$-$C_{40}$-arylalkanes and $C_8$-$C_{40}$-arylalkenes, wherein in each member of the group, one or more hydrogen atoms can be substituted by halogens, OH, —$NR^6_2$ or —CN and one or more $CH_2$-groups can be substituted by —O—, —S—, —$N(R^6)$—, $PO_2$—, —$SO_2$—, —$C(=O)$—, —$C(=O)$—O— or —$C(=O)$—$N(R^5)$—, and from polymers, which are selected from the group of polymers consisting of poly(meth) acrylates, polyesters, polyurethanes, polyethers, polyamides, polycarbonates and polyolefins, wherein $R^5$ is hydrogen, $C_1$-$C_4$ alkyl or phenyl, preferably hydrogen, and wherein $R^6$ is hydrogen, $C_1$-$C_4$ alkyl or phenyl.

An inventive compound of formula (I) may be characterized in that n is 2, 3 or 4, more preferably 2 or 3, in particular 2, m is 0, Z is a chemical single bond or a divalent organic group selected from the group of elements consisting of —$CH_2$—, —$C(=O)$—, —$C(=O)$—O— and —$C(=O)$—$N(R^5)$—, A is a n-valent organic group, which is derived from an organic compound selected from the group consisting of $C_1$-$C_{12}$-alkanes, saturated $C_3$-$C_{60}$-heterocycles, aromatic $C_6$-$C_{40}$-hydrocarbons, $C_2$-$C_{40}$-heteroarenes and $C_7$-$C_{30}$-arylalkanes, wherein in each member of the group, one or more hydrogen atoms can be substituted by halogens, OH, —$NR^6_2$ or —CN and one or more $CH_2$-groups can be substituted by —O—, —S—, —$N(R^6)$—, $PO_2$—, —$SO_2$—, —$C(=O)$—, —$C(=O)$—O— or —$C(=O)$—$N(R^5)$—, and from polymers, which are selected from the group of polymers consisting of poly(meth) acrylates, polyesters, polyurethanes, polyethers, polyamides, polycarbonates and polyolefins, wherein $R^5$ is hydrogen, $C_1$-$C_4$ alkyl or phenyl, preferably hydrogen, and wherein $R^6$ is $C_1$-$C_4$ hydrogen, alkyl or phenyl.

In one embodiment of the present invention, the inventive compound of formula (I) is characterized in that the compound of formula (I) is selected from the group consisting of

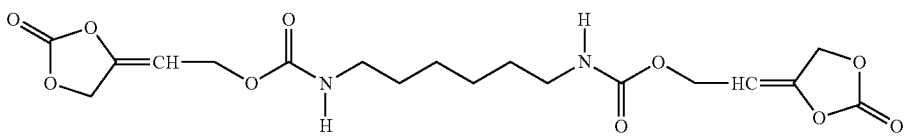

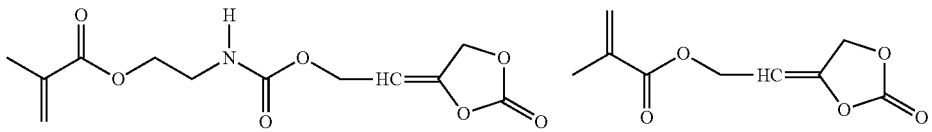

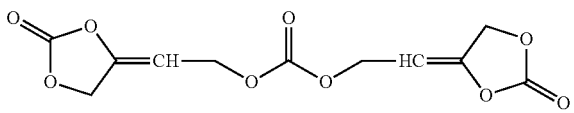

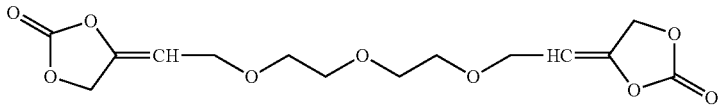

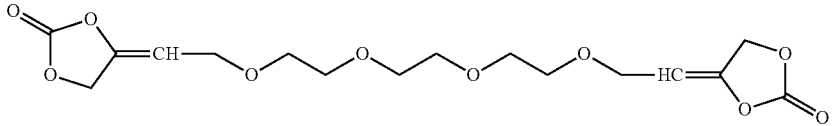

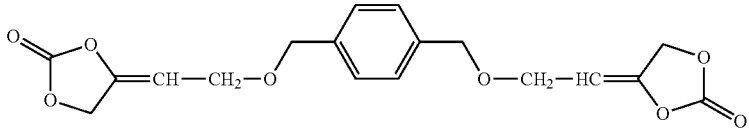

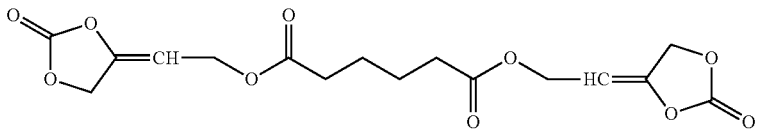

-continued
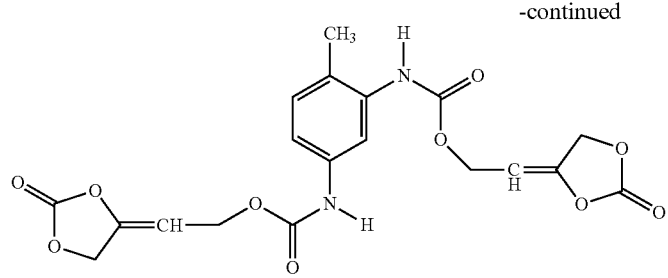
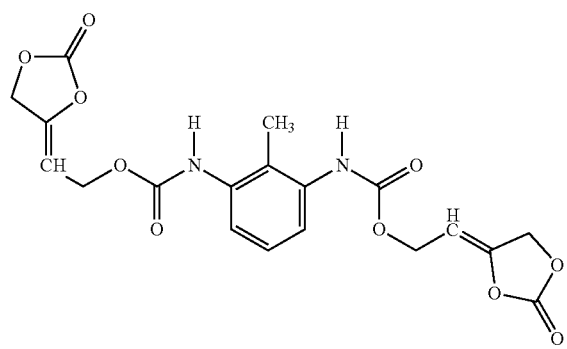
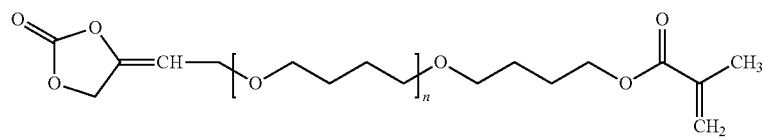
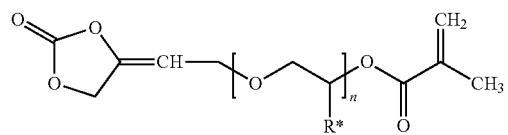
R* = H or Me
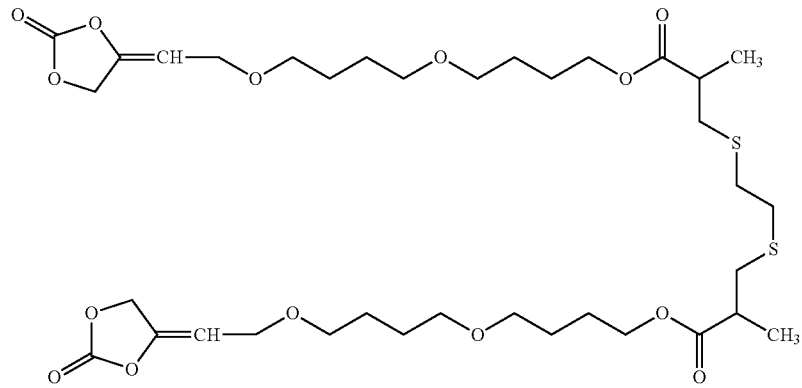
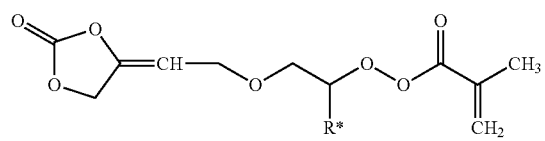
R* = H or CH

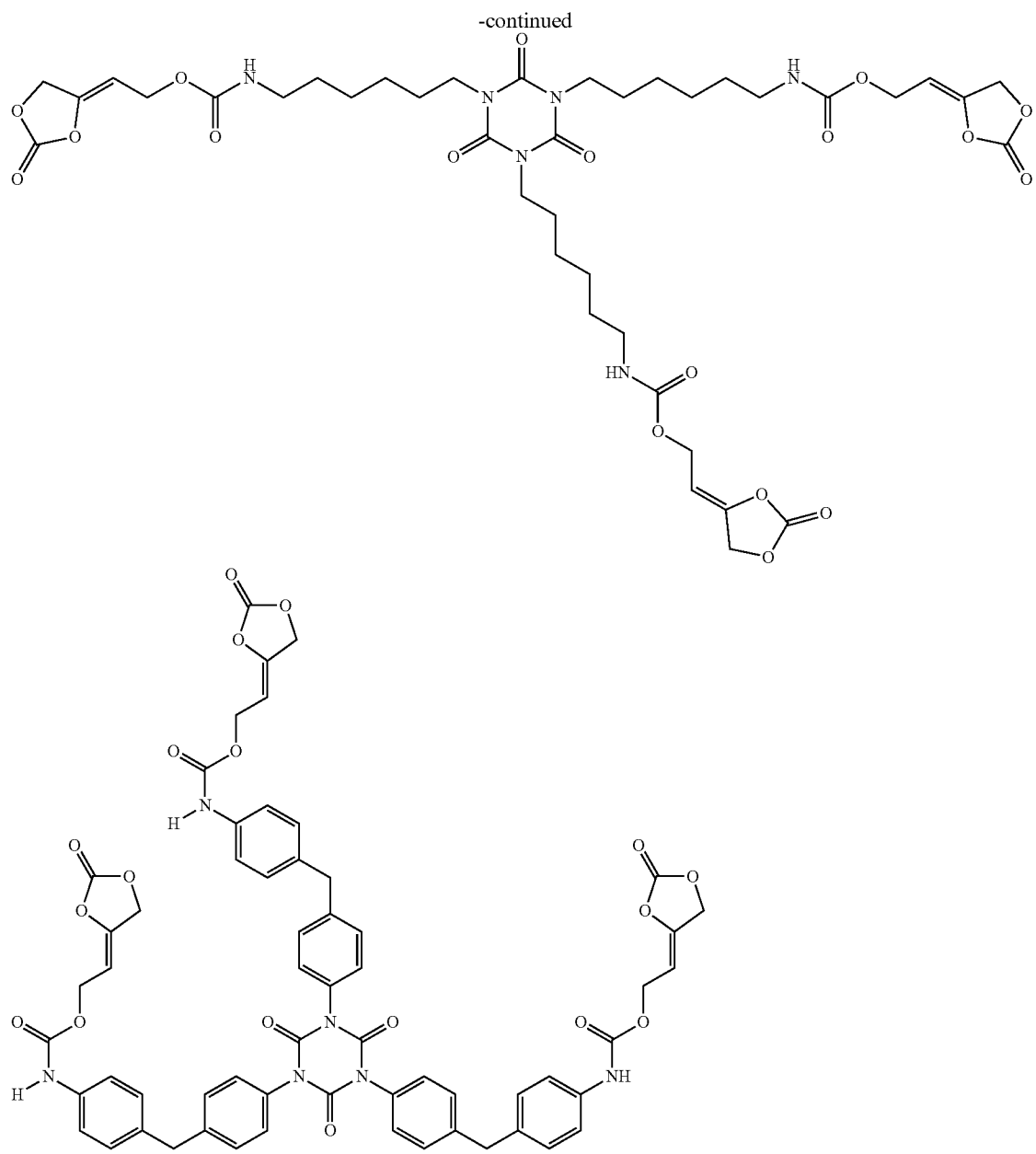

The compounds of formula (I) comprise one or more functional groups of the formula (Ia),

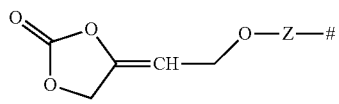

(Ia)

wherein the functional group of the formula (Ia) stands for the respective cis-isomer or trans-isomer or in case that more than one functional group of the formula (Ia) are present in the compound of formula (I), formula (Ia) stands also for a mixture of said cis-trans isomers.

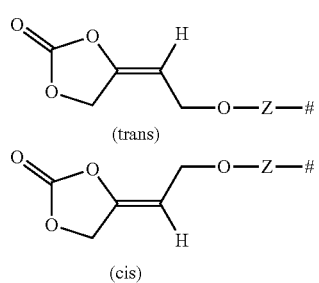

(trans)

(cis)

The inventive compounds of formula (I) can be prepared from starting materials which are based on easily accessible 4-oxy-but-2-yn-1-ol derivatives, preferably based on 1,4-butynediol, wherein the functional group of the formula (Ia) is obtained by a reaction of the functional group of formula (IIa), wherein Z and # are defined as described above, with carbon dioxide in the presence of a transition metal catalysts.

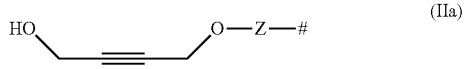
(IIa)

Alternatively, compounds of formula (I), wherein m is 1 or 2, preferably 1, can be polymerized, oligomerized or dimerized by a reaction of the C=C double bond of the functional group of formula (Ib),

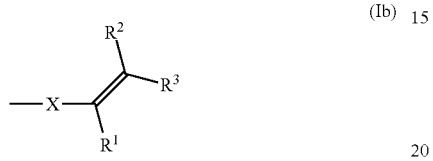
(Ib)

wherein $R^1$, $R^2$, $R^3$ and X have the same meaning as in formula (I) as described above, by forming a new compound of formula (I), wherein m is 0. Examples of suitable reactions of the C=C double bond of the functional group of formula (Ib) are radical polymerization or oligomerization reaction, Diels-Alder-reaction or thiol-ene reaction. Alternatively, reaction with amines could lead to nucleophilic ring opening as well as Michael-type addition towards the double bond (aza-Michael).

Such polymers, oligomers or dimers of formula (I) have a high reactivity compared to compounds having functional groups F from the group of the aliphatic hydroxyl groups, primary and secondary amino groups, phosphine groups, phosphonate groups and mercaptan groups, without having the disadvantages associated with isocyanates. They are therefore particularly suitable as a replacement for polyfunctional isocyanates in numerous applications, especially for 2K binders as described in WO 2013/144299 A1, whereby catalysts may be required for the activation of some functional groups F like activation of hydroxy groups with amines like 1,8-diazabicyclo[5.4.0]undec-7-ene (DBU).

A further aspect of the invention is a process for preparing a compound of formula (I) as described above

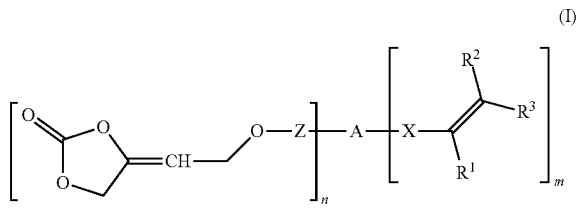
(I)

comprising the process step:
a) reacting a 4-oxy-but-2-yn-1-ol derivative of formula (II)

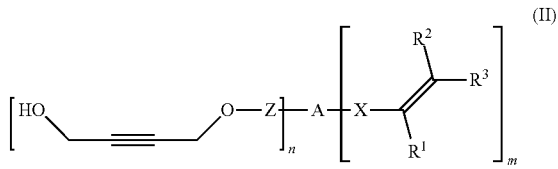
(II)

wherein $R^1$, $R^2$, $R^3$, Z, A, X, n and m have the same meaning as described above, with carbon dioxide in the presence of at least one transition metal catalyst TMC1, which comprises a transition metal selected from metals of groups 10, 11 and 12 of the periodic table of the elements according to IUPAC and at least one bulky ligand selected from the group of ligands consisting of compounds of formula (III) and compounds of formula (IV)

(III)

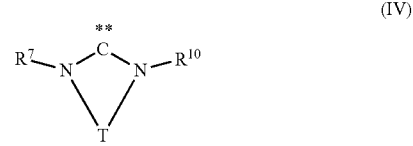
(IV)

wherein
D is P, As or Sb,
$R^7$ is an organic radical having from 1 to 40 carbon atoms,
$R^8$, $R^9$ are identical or different, and are each an organic radical having from 1 to 40 carbon atoms, and,
$R^{10}$ is an organic radical having from 1 to 40 carbon atoms or is identical to $R^7$, and
T is a divalent bridging group selected from —$CR^{12}$=$CR^{13}$—, —$CR^{12}$=N—, —$CR^{12}R^{14}$—$CR^{13}R^{15}$— and —$CR^{12}R^{14}$—$CR^{13}R^{15}$—$CR^{16}R^{17}$—, wherein $R^{12}$, $R^{13}$, $R^{14}$, $R^{15}$, $R^{16}$ and $R^{17}$ are independently from each other hydrogen or as defined as $R^{10}$ or two adjacent radicals $R^{12}$ and $R^{13}$ and/or $R^{15}$ and $R^{16}$ together with the atoms connecting them form a monocyclic or polycyclic, substituted or unsubstituted, aliphatic or aromatic ring system which has from 4 to 40 carbon atoms and can also comprise at least one heteroatom selected from the group consisting of the elements Si, Ge, N, P, O and S.

The inventive process may be characterized in that
D is P,
$R^7$ is a $C_3$ to $C_{40}$ cycloalkyl radical, a $C_2$ to $C_{40}$ heterocycloalkyl radical, a $C_6$ to $C_{40}$ aryl radical or a $C_2$ to $C_{40}$ heteroaromatic radical, preferably a $C_6$ to $C_{40}$ aryl radical or a $C_2$ to $C_{40}$ heteroaromatic radical, wherein $R^7$ is substituted in at least one of the two ortho positions relative to P or N with a radical $R^{11}$, which is an organic radical having from 1 to 40 carbon atoms, a halogen, in particular Cl or Br, hydroxy, $SO_3H$ or nitro or wherein $R^{11}$ together with an adjacent radical substituting $R^7$ in the meta position forms together with the atoms connecting them a monocyclic or polycyclic, substituted or unsubstituted, aliphatic or aromatic ring system, which has from 4 to 40 carbon atoms and can also comprise at least one heteroatom selected from the group consisting of the elements Si, Ge, N, P, O and S, preferably N and O,
$R^8$, $R^9$, $R^{10}$ and T are defined as described above.

In the process of the invention, the 4-oxy-but-2-yn-1-ol derivative of formula (II) is reacted with carbon dioxide in the presence of at least one transition metal catalyst TMC1. Transition metal catalyst TMC1 comprises a transition metal selected from metals of groups 10, 11 and 12 of the periodic table of the elements according to IUPAC, such as Ni, Pd, Pt, Cu, Ag, Au, Zn, Cd and Hg, preferably selected from Cu, Ag and Au, more preferably selected from Cu or Ag, in particular Ag.

The inventive process may be characterized in that the transition metal of transition metal catalyst TMC1 is Ag The transition metal catalyst TMC1 of the process of the invention can be employed in the form of a preformed metal complex which comprises a transition metal and at least one bulky ligand selected from the group of ligands consisting of compounds of formula (III) and compounds of formula (IV), preferably compounds of formula (III), as shown above. Alternatively, the transition metal catalyst TMC1 is formed in situ in the reaction medium by combining a metal compound, herein also termed pre-catalyst, which does not comprise any bulky ligand, with one or more suitable bulky ligand to form a catalytically active metal complex, the transition metal catalyst TMC1, in the reaction medium. In case the bulky ligand is a N-heterocyclic carbene ligand (NHC-ligand) of formula (IV), it is also possible that the transition metal catalyst TMC1 is formed in situ in the reaction medium by combining a pre-catalyst with one or more NHC-precursor, in particular the protonated form of a NHC-ligand, which is in situ converted to the corresponding NHC-ligand of formula (IV), to form a catalytically active metal complex in the reaction medium.

The inventive process may be characterized in that the transition metal catalyst TMC1 is prepared in situ by using a transition metal compound, which does not comprise any bulky ligand, the compound of formula (III) or formula (IV) as bulky ligand or the protonated form of the compound of formula (IV) represented by formula (V),

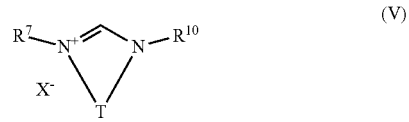

wherein $R^7$, $R^{10}$ and T are defined as described above and $X^-$ is an anion equivalent, together with a base.

Suitable bases for deprotonating the protonated form of different NHC ligands according to formula (V) are described by de Frémont et al., Coordination Chemistry Reviews 253 (2009) 876 to 881. The deprotonation of the protonated forms of NHC ligands can be carried out in ammonia or in non-protic solvents such as THF or ethers. The deprotonation requires anhydrous conditions and the use of strong bases, with $pK_a$ values above 14. Usually, potassium or sodium hydride with a catalytic amount of tert-butoxide is employed, but tert-butoxide itself, lithium aluminum hydride, n-butyllithium, MeLi, t-BuLi, potassium hexamethyldisilazide (KHMDS) and 1,8-diazabicyclo [5.4.0]undec-7-ene (DBU) are also efficient alternatives.

Suitable pre-catalysts are selected from neutral metal complexes, oxides and salts of metals of groups 10, 11 and 12 of the periodic table of the elements. Preferred pre-catalysts are selected from metal complexes, oxides and salts of copper, silver and gold, in particular silver.

Silver compounds that are useful as pre-catalyst are, for example Ag(OAc), AgF, $AgNO_3$, silver trifluoroacetate, $Ag_2O$, $Ag_2CO_3$.

The inventive process may be characterized in that the transition metal compound, also called pre-catalyst, is selected from AgOAc, AgF, $Ag_2O$ and $Ag_2CO_3$.

In addition to the transition metal, the transition metal catalyst TMC1 comprises at least one bulky ligand selected from the group of ligands consisting of compounds of formula (III) and compounds of formula (IV, preferably compounds of formula (III).

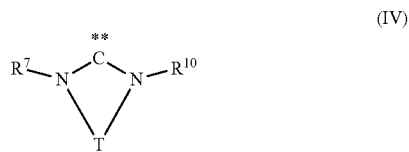

In case the bulky ligand is a compound of formula (III),

the variables are preferably defined as follows:

D is P, As or Sb, preferably P or As, in particular P, $R^7$ is an organic radical having from 1 to 40 carbon atoms, preferably from 2 to 40 carbon atoms, preferably comprising at least one cyclic ring, more preferably $R^7$ is a $C_3$ to $C_{40}$ cycloalkyl radical, a $C_2$ to $C_{40}$ heterocycloalkyl radical, a $C_6$ to $C_{40}$ aryl radical, a $C_2$ to $C_{40}$ heteroaromatic radical, a $C_3$ to $C_{40}$ cycloalkoxy radical, a $C_2$ to $C_{40}$ heterocycloalkoxy radical, a $C_6$ to $C_{40}$ aryloxy radical, a $C_2$ to $C_{40}$ hetaryloxy radical, even more preferably $R^7$ is a $C_3$ to $C_{40}$ cycloalkyl radical, a $C_2$ to $C_{40}$ heterocycloalkyl radical, a $C_6$ to $C_{40}$ aryl radical or a $C_2$ to $C_{40}$ heteroaromatic radical, preferably a $C_6$ to $C_{40}$ aryl radical or a $C_2$ to $C_{40}$ heteroaromatic radical, wherein $R^7$ is substituted in at least one of the two ortho positions relative to D with a radical $R^{11}$, which is an organic radical having from 1 to 40 carbon atoms, preferably a $C_6$ to $C_{40}$ aryl radical, a $C_1$ to $C_{10}$ alkoxy radical or a $C_2$ to $C_{12}$ dialkyl amino radical or wherein $R^{11}$ together with an adjacent radical substituting $R^7$ in the meta position forms together with the atoms connecting them a monocyclic or polycyclic, substituted or unsubstituted, aliphatic or aromatic ring system, which has from 4 to 40 carbon atoms and can also comprise at least one heteroatom selected from the group consisting of the elements Si, Ge, N, P, O and S, preferably N, O and S, and $R^8$, $R^9$ are identical or different, preferably identical, and are each an organic radical having from 1 to 40 carbon atoms, preferably $C_3$ to $C_{20}$ cyclic or acyclic alkyl, in particular tert.-butyl or cyclohexyl, or $C_6$ to $C_{14}$ aryl, in particular phenyl.

In case the bulky ligand is a compound of formula (IV),

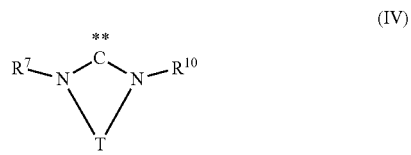
(IV)

the variables are preferably defined as follows:

$R^7$ is an organic radical having from 1 to 40 carbon atoms, preferably from 2 to 40 carbon atoms, preferably comprising at least one cyclic ring,
  more preferably $R^7$ is a $C_6$ to $C_{40}$ aryl radical or a $C_2$ to $C_{40}$ heteroaromatic radical, preferably wherein $R^7$ is substituted in at least one of the two ortho positions relative to N with a radical $R^{11}$, which is an organic radical having from 1 to 40 carbon atoms, preferably a $C_1$ to $C_{10}$ alkyl radical, in particular isopropyl, $R^{10}$ is an organic radical having from 1 to 40 carbon atoms or is identical to $R^7$, preferably $R^{10}$ is identical to $R^7$, and T is a divalent bridging group selected from $-CR^{12}=CR^{13}-$, $-CR^{12}=N-$, $-CR^{12}R^{14}-CR^{13}R^{15}-$ and $-CR^{12}R^{14}-CR^{13}R^{15}-CR^{16}R^{17}-$, preferably $-CR^{12}=CR^{13}-$ and $-CR^{12}R^{14}-CR^{13}R^{15}-$, wherein $R^{12}$, $R^{13}$, $R^{14}$, $R^{15}$, $R^{16}$ and $R^{17}$ are independently from each other hydrogen or as defined as $R^{10}$, preferably hydrogen, or two adjacent radicals $R^{12}$ and $R^{13}$ and/or $R^{15}$ and $R^{16}$ together with the atoms connecting them form a monocyclic or polycyclic, substituted or unsubstituted, aliphatic or aromatic ring system which has from 4 to 40 carbon atoms and can also comprise at least one heteroatom selected from the group consisting of the elements Si, Ge, N, P, O and S The inventive process may be characterized in that the bulky ligand is a compound of formula (III).

The inventive process may be characterized in that the bulky ligand is a compound of formula (III)

(III)

wherein the variables are defined as follows:
D is P,
$R^7$ is a $C_6$ to $C_{40}$ aryl radical or a $C_2$ to $C_{40}$ heteroaromatic radical, wherein $R^7$ is substituted in at least one of the two ortho positions relative to D with a radical $R^{11}$, which is a $C_6$ to $C_{40}$ aryl radical, a $C_1$ to $C_{10}$ alkoxy radical, in particular methoxy, ethoxy, isopropoxy or cyclohexyloxy, or a $C_2$ to $C_{12}$ dialkyl amino radical, in particular dimethyl amino, diethyl amino, di-isopropyl amino, N-morpholinyl or N-piperidyl, or wherein $R^{11}$ together with an adjacent radical substituting $R^7$ in the meta position forms together with the atoms connecting them a monocyclic or polycyclic, substituted or unsubstituted, aliphatic or aromatic ring system, which has from 4 to 40 carbon atoms and can also comprise at least one heteroatom selected from the group consisting of the elements Si, Ge, N, P, O and S, preferably N, O and S, and
$R^8$, $R^9$ are identical or different, preferably identical, and are each an organic radical having from 1 to 40 carbon atoms, preferably $C_3$ to $C_{20}$ cyclic or acyclic alkyl, in particular tert.-butyl, adamantyl or cyclohexyl, or $C_6$ to $C_{14}$ aryl, in particular phenyl.

The inventive process may be characterized in that the bulky ligand is selected from a compound of formulas A to P and mixtures thereof, preferably a compound of formulas A to D and mixtures thereof.

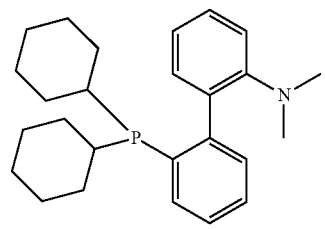
A

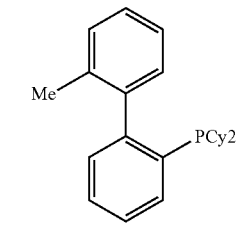
B

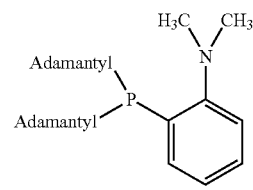
C

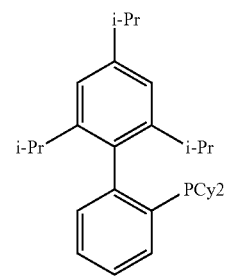
D

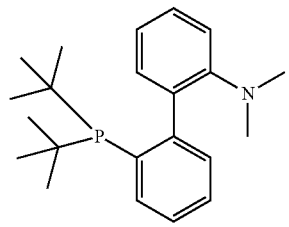
E

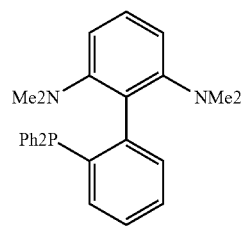
F

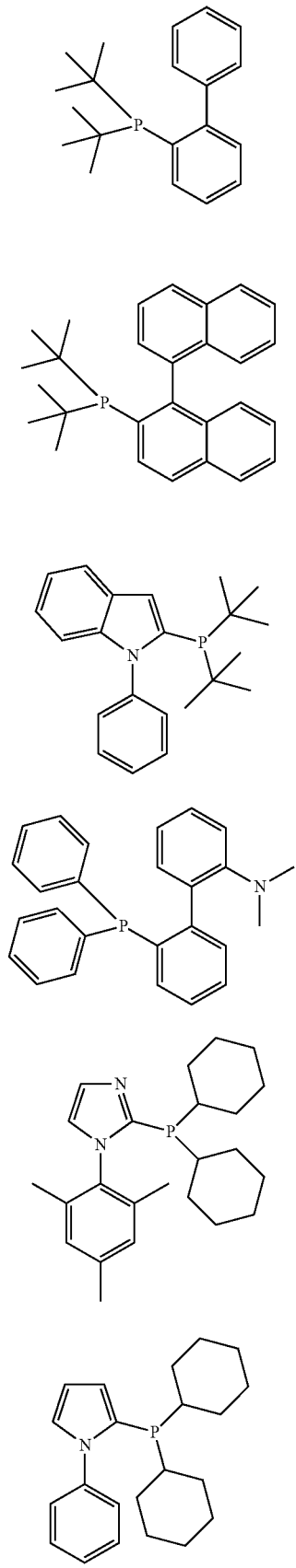

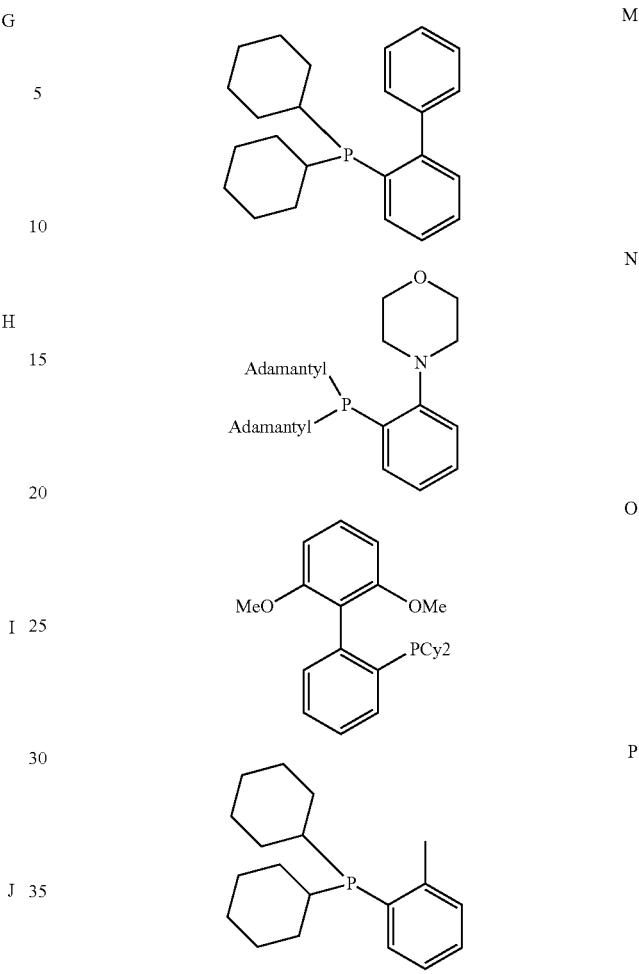

The molar ratio of the bulky ligand to the transition metal of transition metal catalyst TMC1 can be varied in wide range. Preferably the molar ratio of the bulky ligand to the transition metal is below 2. More preferably the ratio of the bulky ligand to the transition metal is in the range from 0.2 to 1.8, even more preferably in the range from 0.3 to 1.5, in particular in the range from 0.4 to 1.2.

The inventive process may be characterized in that the molar ratio of the bulky ligand to the transition metal of transition metal catalyst TMC1 is in the range from 0.4 to 1.2.

In the inventive process the amount of transition metal catalyst TMC1 used in process step a) based on the amount of 4-oxy-but-2-yn-1-ol derivative of formula (II) can be varied in a wide range. Usually the transition metal catalyst TMC1 is used in a sub-stoichiometric amount relative to the 4-oxy-but-2-yn-1-ol derivative of formula (II). Typically, the amount of transition metal catalyst TMC1 is not more than 50 mol %, frequently not more than 20 mol % and in particular not more than 10 mol % or not more than 5 mol %, based on the amount of 4-oxy-but-2-yn-1-ol derivative of formula (II). An amount of transition metal catalyst TMC1 of from 0.001 to 50 mol %, frequently from 0.001 mol % to 20 mol % and in particular from 0.005 to 5 mol %, based on the amount the 4-oxy-but-2-yn-1-ol derivative of formula (II) is preferably used in the process of the invention. Preference is given to using an amount of transition metal catalyst TMC1 of from 0.01 to 5 mol %. All amounts of transition metal complex catalyst indicated are calculated as transition metal and based on the amount of 4-oxy-but-2-yn-1-ol derivative.

The inventive process may be characterized in that the amount of transition metal catalyst TMC1 used in process step a) based on the amount of 4-oxy-but-2-yn-1-ol derivative of formula (II) is in the range from 0.005 to 5 mol %.

The reaction can principally be performed according to all processes known to a person skilled in the art which are suitable for the reaction of primary propargylic alcohols with $CO_2$.

The $CO_2$ used for the carboxylation-cyclization reaction can be used in pure form or, if desired, also in the form of mixtures with other, preferably inert gases, such as nitrogen or argon. Preference is given to using $CO_2$ in undiluted form.

The reaction is typically carried at a $CO_2$ pressure in the range from 0.1 to 200 bar, preferably in the range from 1 to 50 bar, more preferably in the range from 1 to 40 bar.

The inventive process may be characterized in that the process step a) is performed at a pressure in the range from 1 to 50 bar, more preferably in the range from 1 to 40 bar.

The reaction can principally be performed continuously, semi-continuously or discontinuously. Preference is given to a continuous process.

The reaction can principally be performed in all reactors known by a person in the art for this type of reaction and therefore, will select the reactors accordingly. Suitable reactors are described and reviewed in the relevant prior art, e.g. appropriate monographs and reference works such as mentioned in U.S. Pat. No. 6,639,114 B2, column 16, line 45-49. Preferably, for the reaction an autoclave is employed which may have an internal stirrer and an internal lining such as a Teflon lining.

The composition obtained in the carboxylation-cyclization reaction of the present invention comprises a compound of formula (I), which comprises at least one 4-(2-oxyethylidene)-1,3-dioxolan-2-one unit.

Process step a) of the inventive process can be performed in a wide temperature range. Preferably process step a) is performed at a temperature in the range from 0° C. to 150° C. and particularly preferably in the range from 10° C. to 80° C. Temperatures below 100° C. have surprisingly been found to be particularly advantageous.

The inventive process may be characterized in that the process step a) is performed at a temperature in the range from 0° C. to 100° C., preferably in the range from 10° C. to 80° C.

The process of the invention can be carried out in the presence of a solvent. Suitable solvents are selected from aliphatic hydrocarbons, aromatic hydrocarbons, halogenated hydrocarbons, amides, ureas, nitriles, sulfoxides, sulfones, esters, carbonates, ethers, alcohols and mixtures thereof. Preferred solvents are
aliphatic hydrocarbons such as pentane, hexane, heptane, octane or cyclohexane;
aromatic hydrocarbons such as benzene, toluene, xylenes, ethylbenzene, mesitylene or benzotrifluoride;
halogenated hydrocarbons such as dichloromethane,
amides such as dimethylformamide, diethylformamide, N-methylpyrrolidone, N-ethylpyrrolidone or dimethylacetamide;
ureas such as tetramethylurea, N,N-dimethylimidazolinone (DMI) and N,N-dimethylpropyleneurea (DMPU);
nitriles such as acetonitrile or propionitrile;
sulfoxides such as dimethyl sulfoxide;
sulfones such as sulfolane;
esters such as methyl acetate, ethyl acetate, t-butyl acetate;
carbonates such as diethyl carbonate, ethylene carbonate and propylene carbonate; and
ethers such as dioxane, tetrahydrofuran, diethyl ether, dibutyl ether, methyl t-butyl ether, diisopropyl ether or diethylene glycol dimethyl ether;
If desired, mixtures of two or more of the afore-mentioned solvents can also be used.

Preference is given to using dichloromethane, acetone, dimethylformamide or acetonitrile as solvents.

The inventive process may be characterized in that the reaction is carried out in the presence of a solvent selected from aliphatic hydrocarbons, aromatic hydrocarbons, halogenated hydrocarbons, amides, ureas, nitriles, sulfoxides, sulfones, esters, carbonates, ethers, alcohols and mixtures thereof, preferably selected from dichloromethane, acetone, dimethylformamide or acetonitrile.

Alternatively, the process of the invention can be carried out in the absence of any of the above-mentioned organic solvent, so-called neat conditions, preferably in the presence of liquid or supercritical carbon dioxide, in particular in the presence of supercritical carbon dioxide.

Alternatively, the process of the invention can be carried out in the presence of liquid or supercritical carbon dioxide, in particular in the presence of supercritical carbon dioxide, which is mixed with one of the above-mentioned organic solvent, so-called $CO_2$-expanded solvents.

The composition obtained in the carboxylation-cyclisation of the invention comprises the compound of formula (I), which is a compound comprising at least one 4-(2-oxyethylidene)-1,3-dioxolan-2-one unit.

The work-up of the reaction mixture of the inventive process and the isolation of the compound of formula (I) are effected in a customary manner, for example by filtration, an aqueous extractive work-up or by a distillation, for example under reduced pressure. The compound of formula (I) may be obtained in sufficient purity by applying such measures or a combination thereof, obviating additional purification steps. Alternatively, further purification can be accomplished by methods commonly used in the art, such as chromatography.

The inventive process may be characterized in that the compound of formula (I) is separated from the transition metal catalyst TMC1 after process step a) via distillation, extraction, precipitation or chromatography.

The inventive process may be characterized in that the transition metal catalyst TMC1 is recycled to the reaction step a) after the compound of formula (I) is removed via distillation, extraction, precipitation or chromatography.

Alternatively, the inventive compounds of formula (I) can be prepared by reacting 4-(2-hydroxyethylidene)-1,3-dioxolan-2-one (VIa) with an appropriate linker, which comprises one or more functional groups capable to react with the hydroxy group of the alcohol of formula (VIa) to obtain a compound of formula (I).

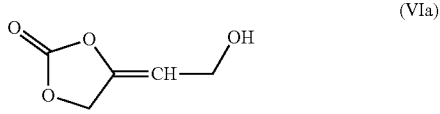

(VIa)

The alcohol of formula (VIa), 4-(2-hydroxyethylidene)-1,3-dioxolan-2-one is directly available by the reaction of 1,4-butynediol with carbon dioxide in the presence of at least one transition metal catalyst TMC1 as described in detail above or as described in EP application No 17186136.2. Derivatives of the alcohol of formula (VIa) are easily available, wherein the hydroxy group OH is substituted by an ether-hydroxy group —O-J-OH, as subsequently explained.

A further aspect of the invention is a process for preparing a compound of formula (I) as described above

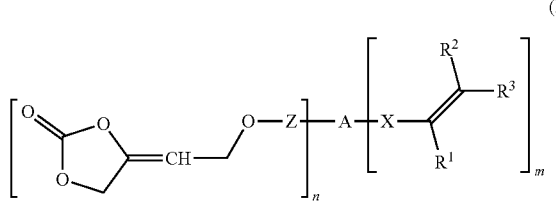
(I)

comprising the process step:
b) reacting an alcohol of formula (VI)

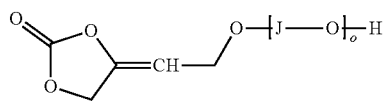
(VI)

with a compound of formula (VII)

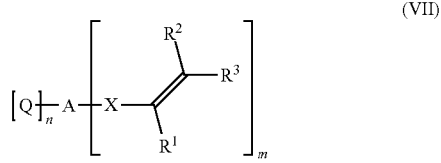
(VII)

wherein $R^1$, $R^2$, $R^3$, A, X, n and m have the same meaning as in formula I, and
wherein
J is a divalent organic group having from 1 to 100 carbon atoms, preferably 1 to 40 carbon atoms,
Q is a functional group capable to react with the hydroxy group of the alcohol of formula (VI) in an addition reaction under formation of a —O-Q(—H)-A unit or Q is a leaving group substituted by the oxygen of the hydroxy group of the alcohol of formula (VI) under formation of H-Q, and
o is 0 or 1.

J is a divalent organic group having from 1 to 100 carbon atoms, preferably 1 to 40 carbon atoms. Preferably J is a divalent organic group derived from an organic compound selected from the group consisting of $C_1$-$C_{40}$-alkanes, $C_1$-$C_{40}$-alkenes, saturated $C_3$-$C_{20}$-heterocycles, aromatic $C_6$-$C_{40}$-hydrocarbons, $C_2$-$C_{40}$-heteroarenes, $C_7$-$C_{40}$-arylalkanes and $C_8$-$C_{40}$-arylalkenes, wherein in each member of the group, one or more hydrogen atoms can be substituted by halogens, OH, —$NR^6_2$ or —CN, and one or more $CH_2$-groups can be substituted by —O—, —S—, —N($R^6$)—, $PO_2$—, —$SO_2$—, —C(=O)—, —C(=O)—O— or —C(=O)—N($R^5$), wherein $R^5$ is hydrogen, $C_1$-$C_4$ alkyl or phenyl, preferably hydrogen, and wherein $R^6$ is hydrogen, $C_1$-$C_4$ alkyl or phenyl. More preferably, J is a divalent organic group derived from an organic compound selected from the group consisting of $C_1$-$C_{40}$-alkanes, wherein one or more $CH_2$-groups can be substituted by —O—.

Preferred, but not limiting examples of J are —$CH_2$—, —$CH_2$—$CH_2$—, —$CH_2$—C(MeH)—, —($CH_2$)$_4$—, —($CH_2$)$_6$—, —$CH_2$—$C_6H_6$—$CH_2$—, —($CH_2$—O)$_{1-20}$—$CH_2$—, —($CH_2$—$CH_2$—O)$_{1-20}$—$CH_2$—$CH_2$—, —($CH_2$—C(MeH)—O)$_{1-20}$—$CH_2$—C(MeH)— or —(($CH_2$)$_4$—O—)$_{1-20}$—($CH_2$)$_4$—, in particular —$CH_2$—$CH_2$—, —$CH_2$—C(MeH)—, —($CH_2$)$_4$—, —($CH_2$—$CH_2$—O)$_{1-3}$—$CH_2$—$CH_2$—, —($CH_2$—C(MeH)—O)$_{1-3}$—$CH_2$—C(MeH)— or —(($CH_2$)$_4$—O—)$_{1-3}$—($CH_2$)$_4$—. The index range 1-3 stands for the indices 1, 2 or 3 and the index range 1-20 stands for the indices 1, 2, 3, 4, 5, 6, 7, 8, 9, 10, 11, 12, 13, 14, 15, 16, 17, 18, 19 or 20.

Suitable functional groups Q, which are capable to react with a primary or secondary hydroxy group of the fragment HO—$CH_2$— or HO—CH(Me)- and the corresponding linkers of formula (VII) are known to a person skilled in the art.

The inventive process may be characterized in that

Q is selected from the group of the functional groups consisting of —N=C=O (or derivatives), 2-oxiranyl, —C=N—, C=C=O, halides, preferably Cl, Br or I, and organic sulfonates, preferably tosylate, mesylate, triflate or nonaflate, and OH, $R^aC$(=O)O, $R^aO$ and imidazole, where $R^a$ is $C_1$-$C_4$ alkyl or substituted or unsubstituted phenyl, preferably selected from the group of the functional groups consisting of —N=C=O, Cl, Br and imidazole.

The inventive process may be characterized in that the compound of formula (VII) is selected from the group of compounds consisting of

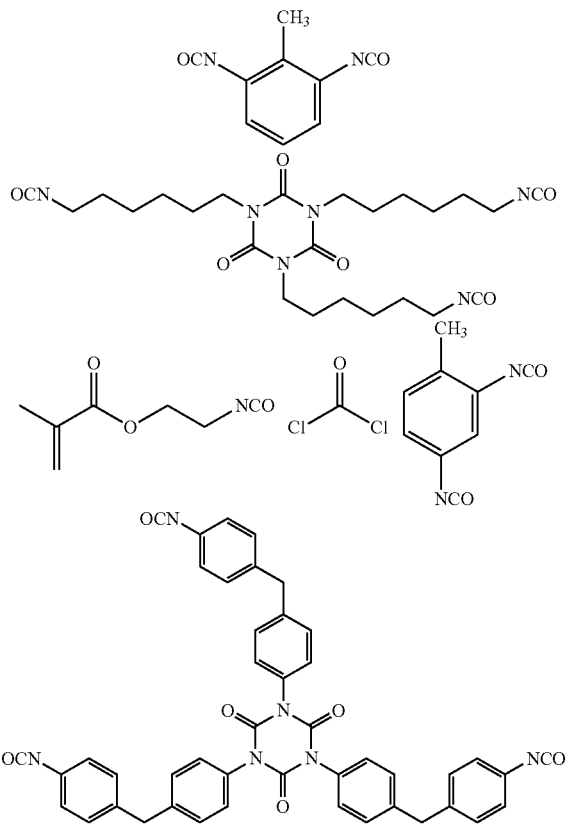

-continued

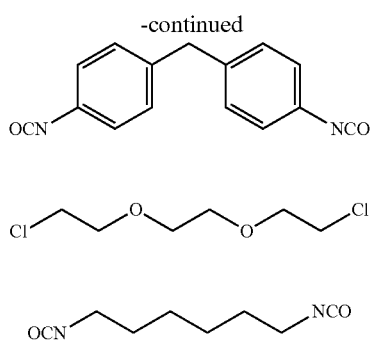

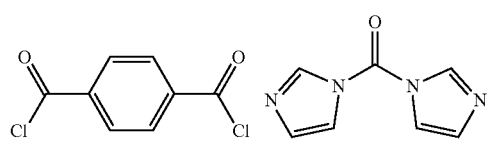

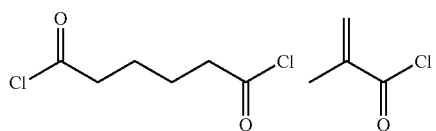

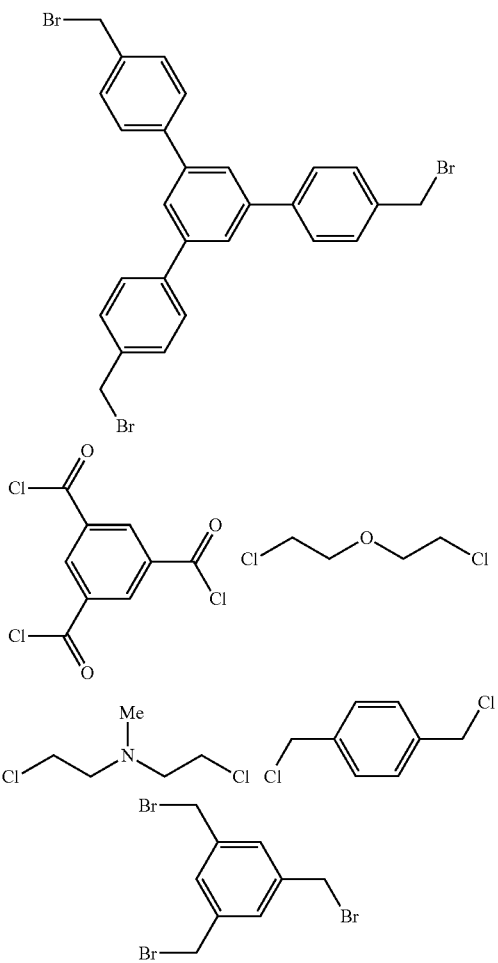

A further aspect of the invention is a compound of formula (II)

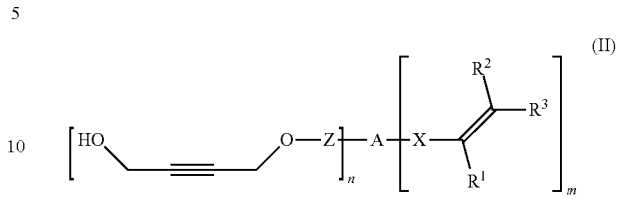

wherein $R^1$, $R^2$, $R^3$, Z, A, X, n and m have the same meaning as in formula I as described above.

Compounds of formula (II) are available by reacting 1,4-butynediol with an appropriate linker, preferably, a compound of formula (VII) as described above. Preferably 1,4-butynediol is mono-functionalized to obtain the compound of formula (II).

Compounds of formula (VII) comprise one or more functional groups Q, which are capable to react with one of the two hydroxy group of 1,4-butynediol to obtain the compound of formula (II). Examples of such functional groups are a polymerizable olefin function, phosgene or derivatives, CDI, carbonates, chloroformiate, a carboxylic acid function and derivates thereof such as an ester, an anhydride function, a ketene or acid chloride function, further an alcohol function, a protected amine function e.g. an imine, an isocyanate function (or derivatives), an alkyl-carbonate function, an uretdione function, an alkyne function, an vinylether function, an epoxy-function, an diimide function, a cyclic carbonate function, vinylene-1,3 dicarbonyl function or another cylic exo-vinylencarbonate function or aldehydes. In case of another exo vinylene carbonate unit, it's preferred to install this group also by using the above mentioned catalytic system and therefor substrates with two 4-oxy-but-2-yn-1-ol derivative functions must be used as the substrate to obtain di-exo vinylene carbonates.

Non-limiting examples of compounds of formula (VII) are for example 2,4-toluendiisocynate, 2,6-toluenediisocyante, 1,6-hexamethylenediisocynate, adipic acid chloride, aromatic acid chlorides such as terephthaloyl chloride, di(m) ethylcarbonate, diphenylcarbonate, alkynes, mono- and difunctional Michael acceptors such as BDO-bis-(meth) acrylate, di(meth)acrylamides, (bis)maleides, divinylether, cyano acrylate, methylene malonate, phosgene, methacrylic acid anhydride, 2-(methacryloxy)ethyl isocyanate, maleic acid anhydride, succinic acid anhydride, bis(2-chloroethyle) ether, bis(2-chloroethyl)amine, 1,4-bis-chloromethylbenzene, 1,4-bis-bromo-momethylbenzene, 1,2-bis-chloromethylbenzene, 1,2-bis-bromo-momethylbenzene, 1,3-bis-chloromethylbenzene, 1,3-bis-bromo-methylbenzene or 1,1-Carbonyldidimidazol. Furthermore, inorganic compounds such as silicates (e.g. via transesterification), sulfates (e.g. via transesterification or addition to divinyl sulfate), sulfonates, phosphates and phosphonates might be used as linker.

In one embodiment of the present invention, the inventive compound of formula (II) is characterized in that the compound of formula (II) is selected from the group consisting of

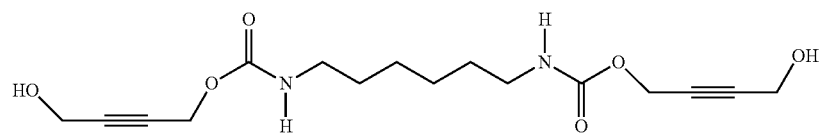
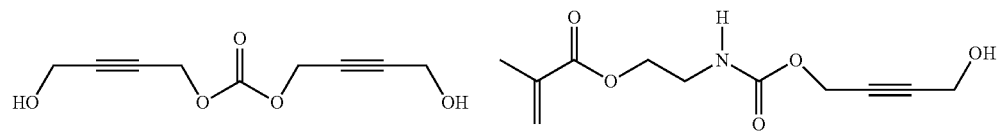
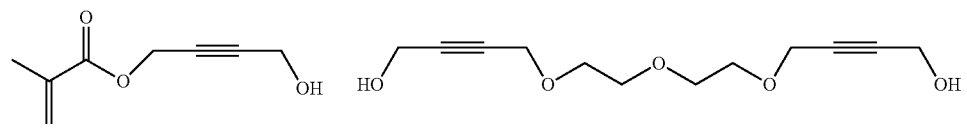
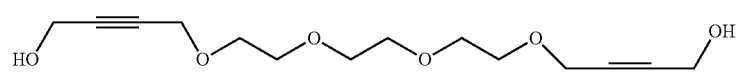
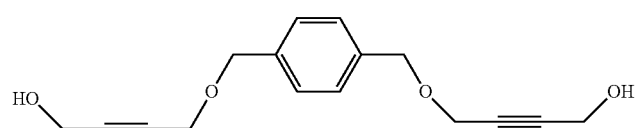
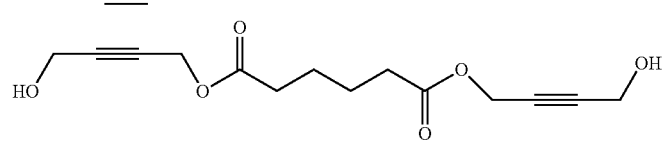
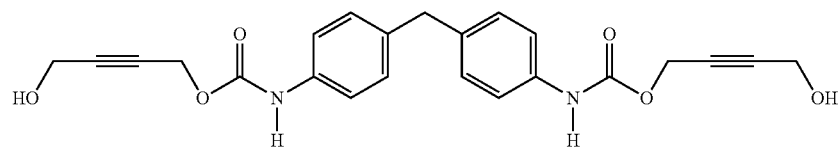
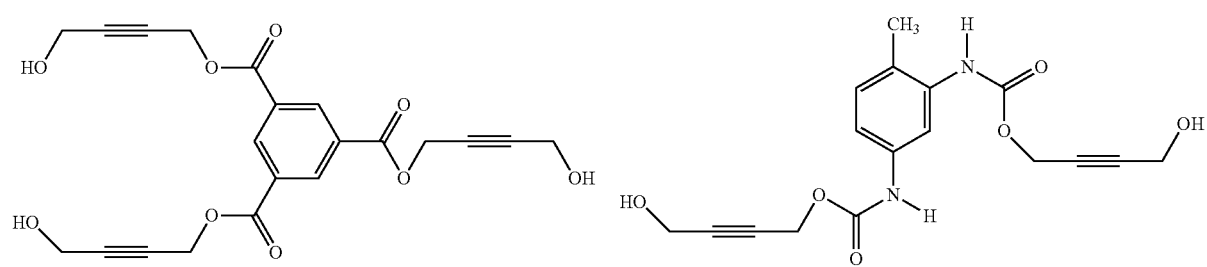
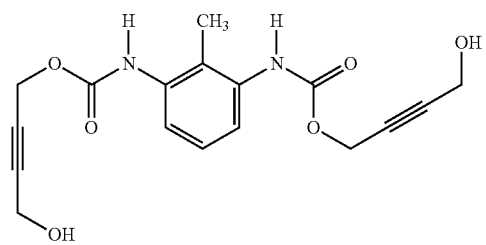
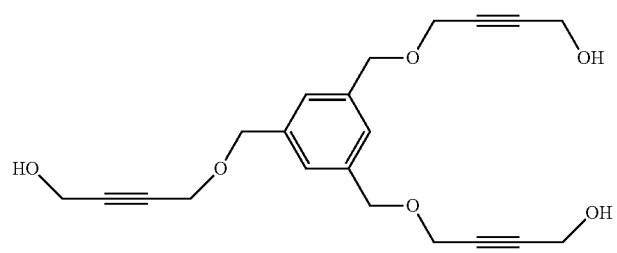

-continued

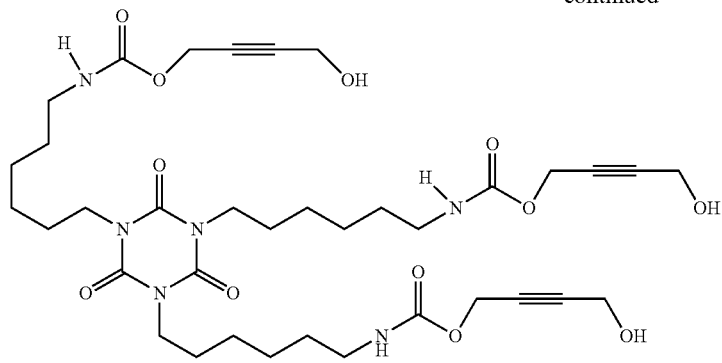

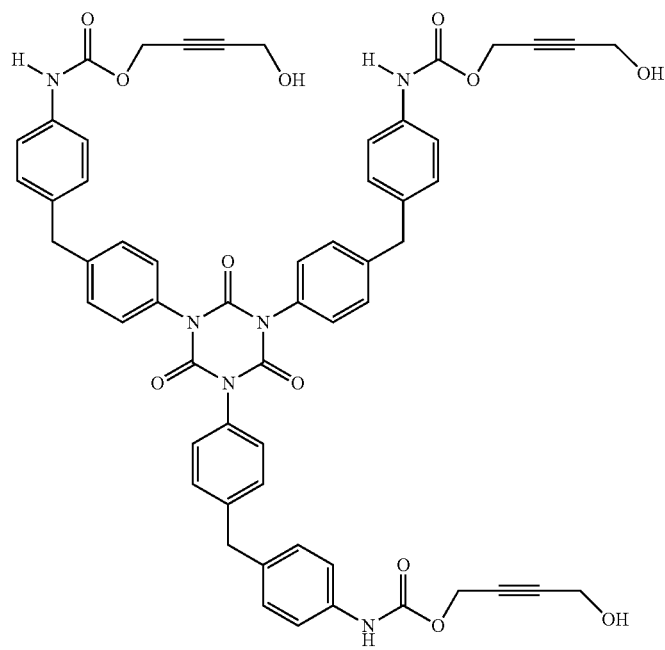

A further aspect of the invention is a process for preparing a compound of formula (II) as described above comprising the process step:
c) reacting the diol 1,4-butynediol of formula (VIII)

(VIII)

with a compound of formula (VII)

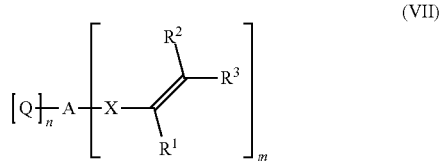
(VII)

wherein $R^1$, $R^2$, $R^3$, A, X, n and m have the same meaning as in formula I, and wherein Q is a functional group capable to react with the hydroxy group of the alcohol of formula (VI) in an addition reaction under formation of a —O-Q(—H)-A unit or Q is a leaving group substituted by the oxygen of the hydroxy group of the alcohol of formula (VI) under formation of H-Q.

Suitable functional groups Q, which are capable to react with a primary hydroxy group of the fragment HO—$CH_2$— and the corresponding linkers of formula (VII) are known to a person skilled in the art and have been described above.

A further aspect of the present invention is the use of 1,4 but-2-in-diol for the preparation of compounds of formula (I), preferably for the preparation of compounds of formula (I) without protecting any functional groups or without using any protection chemistry for functional groups, which are well known to a person skilled in the art.

Alternatively, compounds of formula (II), wherein m is 1 or 2, preferably 1, can be polymerized, oligomerized or dimerized by a reaction of the C=C double bond of the functional group of formula (Ib),

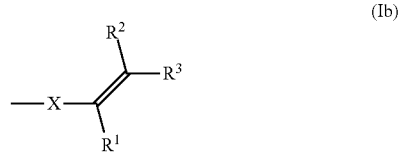

wherein $R^1$, $R^2$, $R^3$ and X have the same meaning as in formula I as described above, by forming a new compound of formula (II), wherein m is 0. Examples of suitable reactions of the C=C double bond of the functional group of formula (Ib) are radical polymerization or oligomerization reaction, Diels-Alder-reaction or thiol-ene reaction.

Compounds of formula (II) can also be prepared in a multi-step synthesis, wherein the HO—CH$_2$— group of the functional group of formula (IIa) of the compound of formula (II),

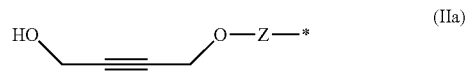

wherein Z and # are defined as described above, is prepared in the final step from the corresponding functional group of formula (IIb).

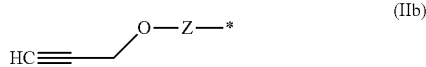

The following scheme shows one possible example of this synthetic strategy.

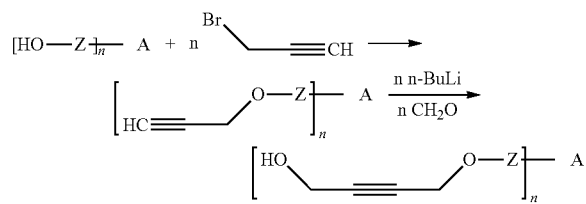

The inventive compounds of formula (I) can be used in the same way as the related higher substituted, more complicated exo-vinylene carbonates as described in the introduction.

Therefore, a further aspect of the present invention is the use of the compound of formula (I) as described above as intermediate or crosslinker or as monomer in polymerization reactions or in oligomerization reactions, in particular in dimerization reactions, in particular, as monomer for the formation of poly(keto urethanes), poly(keto carbonates), poly(keto thiocarbonates), poly(keto ethers) or polymers comprising a mixture of the functional groups selected from the group consisting of keto urethanes, keto carbonates, keto thiocarbonates, keto ethers, polyunsaturated urethanes and polyunsaturated carbonates.

In one embodiment of the present invention, the inventive use of the compound of formula (I) as described above is characterized in that n is 2, 3, 4, 5 or 6, preferably 2, 3 or 4, more preferably 2 or 3, in particular 2, and m is 0 as a monomer in polymerization reactions, in particular, as monomer for the formation of poly(keto urethanes), poly(keto carbonates), poly(keto thiocarbonates), poly(keto ethers) or polymers comprising mixture the functional groups consisting of keto urethanes, keto carbonates, keto thiocarbonates, keto ethers, polyunsaturated urethanes and polyunsaturated carbonates.

A further aspect of the present invention is the use of the compound of formula (I) as described above as reactive component in adhesive or sealing compositions, in compositions for coating materials, e.g. in laminating processes, lacquers, paints, inks, building materials, elastomers, foams or for binding of fibers or particles or engineering plastics.

The inventive compounds of formula (I) can be used together with a polyfunctional hardener as a second component in two component bonding agent systems, also called two pack adhesives, as described for example in WO 2006/010408, WO 2016/2026652 A1, WO 2017/207461 A1, WO 2018054713 A1 or WO 2018054609 A1. Alternatively, the inventive compounds of formula (I) can be used in one component bonding agent systems, also called one pack adhesives, as described for example in WO 2008110394.

A further aspect of the present invention is a two-component composition comprising as a first component at least one compound of formula (I) as described above, preferably wherein n in formula (I) is 2, 3, 4, 5 or 6, preferably 2, 3 or 4, more preferably 2 or 3, in particular 2, and m is 0, and as a second component at least one multifunctional hardener that comprises at least two functional groups selected from the group consisting of primary amino groups, secondary amino groups, hydroxy groups, phosphine groups, phosphonate groups, carboxy- and mercaptan groups. Preferably, the functional groups of the hardener are selected from aliphatic hydroxyl groups, aliphatic primary amino groups, aliphatic secondary amino groups, aliphatic phosphine groups, aliphatic phosphonate groups and aliphatic mercaptan groups, more preferably selected from aliphatic hydroxyl groups, aliphatic primary amino groups and aliphatic secondary amino groups and respective protected functional groups such as an imine, which liberates the amino group after a reaction with water.

The inventive two-component compositions are also called two-pack adhesives or two-pack binder compositions hereinafter.

The inventive two-component compositions (two-pack binder compositions) may also comprise one or more suitable catalysts for the hardening, which are guided in a known manner by the nature of the reactive functional groups of the multifunctional hardener. The two-pack adhesive is preferably applied either in the form of a solution in an organic solvent or solvent-free. "Solvent-free" means that less than 5% by weight, more preferably less than 2% by weight or zero organic solvent or water is present.

Two-pack adhesives (also called two-pack binder compositions hereinafter) are understood to mean a binder comprising at least two polyfunctional binder constituents which react with one another to form bonds and in doing so form a polymeric network. Due to the alkylidene-1,3-dioxolan-2-one groups present therein, the polymers of the invention can react with numerous nucleophilic groups to form bonds. Examples of such nucleophilic groups are particularly aliphatic hydroxyl groups, aliphatic primary and secondary amino groups, phosphine groups, especially aliphatic phosphine groups, phosphonate groups, especially aliphatic phosphonate groups, and analogous phosphorus compounds, carboxylate group and also mercaptan groups, especially aliphatic mercaptan groups.

Accordingly, two-pack binder compositions comprise, as well as at least one compound of formula (I) of the invention, preferably additionally at least one compound having at least 2 functional groups F, for example 2, 3, 4, 5, 6, 7, 8, 9 or 10 functional groups F, which are selected from aliphatic hydroxyl groups, aliphatic primary or secondary amino groups, aliphatic phosphine groups, aliphatic phosphonate groups, carboxylate group and similar groups, and aliphatic mercaptan groups. These compounds are also referred to hereinafter as hardeners. Preferred functional groups F are aliphatic hydroxyl groups and aliphatic primary and secondary amino groups. Preferably, the amount of hardener is selected such that the molar ratio of functional alkylidene-1,3-dioxolan-2-one groups of the formula I to the functional groups F in the hardener is in the range from 1:10 to 10:1, particularly in the range from 5:1 to 1:5 and especially in the range from 1:2 to 2:1. The compound of formula (I) of the invention can be also mixed with known cyclic exo vinyl carbonates, which react in the same manner as the compounds of formula (I) or with other cyclic carbonates without a vinyl function.

The hardener may be a low molecular weight substance, which means that the molecular weight thereof is below 500 g/mol, or an oligomeric or polymeric substance having a number-average molecular weight above 500 g/mol.

The hardeners preferred in accordance with the invention include aminic hardeners, i.e. hardeners which have at least two primary or secondary amino groups, and alcoholic hardeners, i.e. compounds which have at least two hydroxyl groups.

The aminic hardeners, also amine hardeners hereinafter, include, for example, aliphatic and cycloaliphatic polyamines, aromatic and araliphatic polyamines and polymeric amines, for example amino resin, PEIor polylysine and polyamidoamines. Amine hardeners crosslink polymers having 1,3-dioxolan-2-one groups, also called carbonate polymers hereinafter, by reaction of the primary or secondary amino functions of the polyamines with the 1,3-dioxolan-2-one groups of the carbonate polymers to form urethane functions. Preferred polyamine hardeners have an average of at least two primary or secondary amino groups per molecule, for example two, three or four primary or secondary amino groups per molecule. They may also additionally comprise one or more tertiary amino groups. Suitable polyamines are, for example,

- aliphatic polyamines such as ethylenediamine, 1,2- and 1,3-propanediamine, neopentanediamine, hexamethylenediamine, octamethylenediamine, 1,10-diaminodecane, 1,12-diaminododecane, diethylenetriamine, triethylenetetramine, tetraethylenepentamine, 2,2-dimethylpropylenediamine, trimethylhexamethylenediamine, 1-(3-aminopropyl)-3-aminopropane, 1,3-bis(3-aminopropyl)propane, 4-ethyl-4-methylamino-1-octylamine, and the like;
- cycloaliphatic diamines, such as 1,2-diaminocyclohexane, 1,2-, 1,3-, 1,4-bis(amino-methyl)cyclohexane, 1-methyl-2,4-diaminocyclohexane, N-cyclohexylpropylene-1,3-diamine, 4-(2-aminopropan-2-yl)-1-methylcyclohexane-1-amine, isophoronediamine, 4,4'-diaminodicyclohexylmethane (Dicykan), 3,3'-dimethyl-4,4'-diaminodicyclohexylmethane, 3,3',5,5'-tetramethyl-4,4'-diaminodicyclohexylmethane, 4,8-diaminotricyclo[5.2.1.0]decane, norbornanediamine, menthanediamine, menthenediamine, and the like;
- aromatic diamines, such as tolylenediamine, xylylenediamine, especially meta-xylylenediamine (MXDA), bis(4-aminophenyl)methane (MDA or methylenedianiline), bis(4-aminophenyl) sulfone (also known as DADS, DDS or dapsone), and the like;
- cyclic polyamines, such as piperazine, N-aminoethylpiperazine, and the like;
- polyetheramines, especially difunctional and trifunctional primary polyetheramines based on polypropylene glycol, polyethylene glycol, polybutylene oxide, poly(1,4-butanediol), polytetrahydrofuran (polyTHF) or polypentylene oxide, for example 4,7,10-trioxatridecane-1,3-diamine, 4,7,10-trioxatridecane-1,13-diamine, 1,8-diamino-3,6-dioxaoctane (XTJ-504 from Huntsman), 1,10-diamino-4,7-dioxadecane (XTJ-590 from Huntsman), 1,12-diamino-4,9-dioxadodecane (from BASF SE), 1,3-diamino-4,7,10-trioxatridecane (from BASF SE), primary polyetheramines based on polypropylene glycol having a mean molar mass of 230, for example polyetheramine D 230 (from BASF SE) or Jeffamine® D 230 (from Huntsman), difunctional, primary polyetheramines based on polypropylene glycol having a mean molar mass of 400, e.g. polyetheramine D 400 (from BASF SE) or Jeffamine® XTJ 582 (from Huntsman), difunctional, primary polyetheramines based on polypropylene glycol having a mean molar mass of 2000, for example polyetheramine D 2000 (from BASF SE), Jeffamine® D2000 or Jeffamine® XTJ 578 (each from Huntsman), difunctional, primary polyetheramines based on propylene oxide having a mean molar mass of 4000, for example polyetheramine D 4000 (from BASF SE), trifunctional, primary polyetheramines prepared by reacting propylene oxide with trimethylolpropane followed by an amination of the terminal OH groups, having a mean molar mass of 403, for example polyetheramine T 403 (from BASF SE) or Jeffamine® T 403 (from Huntsman), trifunctional, primary polyetheramine prepared by reacting propylene oxide with glycerol, followed by an amination of the terminal OH groups, having a mean molar mass of 5000, for example polyetheramine T 5000 (from BASF SE) or Jeffamine® T 5000 (from Huntsman), aliphatic polyetheramines formed from a propylene oxide-grafted polyethylene glycol and having a mean molar mass of 600, for example Jeffamine® ED-600 or Jeffamine® XTJ 501 (each from Huntsman), aliphatic polyetheramines formed from a propylene oxide-grafted polyethylene glycol and having a mean molar mass of 900, for example Jeffamine® ED-900 (from Huntsman), aliphatic polyetheramines formed from a propylene oxide-grafted polyethylene glycol and having a mean molar mass of 2000, for example Jeffamine® ED-2003 (from Huntsman), difunctional, primary polyetheramine prepared by amination of a propylene oxide-grafted diethylene glycol, having a mean molar mass of 220, for example Jeffamine® HK-511 (from Huntsman), aliphatic polyetheramines based on a copolymer of poly(tetramethylene ether glycol) and polypropylene glycol having a mean molar mass of 1000, for example Jeffamine® XTJ-542 (from Huntsman), aliphatic polyetheramines based on a copolymer of poly(tetramethylene ether glycol) and polypropylene glycol having a mean molar mass of 1900, for example Jeffamine® XTJ-548 (from Huntsman), aliphatic polyetheramines based on a copolymer of poly(tetramethylene ether glycol) and polypropylene glycol having a mean molar mass of 1400, for example Jeffamine® XTJ-559 (from Huntsman), polyethertriamines based on a butylene oxide-grafted, at least trihydric alcohol having a mean molar mass of 400, for example Jeffamine® XTJ-566 (from Huntsman), aliphatic polyetheramines prepared by amination of butylene oxide-grafted alcohols having a mean molar mass of 219, for example Jeffamine® XTJ-568 (from Huntsman), polyetheramines based on pentaerythritol and propylene oxide having a mean molar mass of 600, for example Jeffamine® XTJ-616 (from Huntsman), polyetheramines based on triethylene glycol having a mean molar mass of 148, for example Jeffamine® EDR-148 (from Huntsman), difunctional, primary polyetheramines prepared by amination of a propylene oxide-grafted ethylene glycol, having a mean molar mass of 176, for example Jeffamine® EDR-176 (from Huntsman), and also polyetheramines prepared by amination of polytetrahydrofuran (polyTHF) having a mean molar mass of 250, for example PolyTHF-amine 350 (BASF SE), and mixtures of these amines;

polyamidoamines (amidopolyamines), which are obtainable by reaction of dimeric fatty acids (for example dimeric linoleic acid) with polyamines of low molecular weight, such as diethylenetriamine, 1-(3-aminopropyl)-3-aminopropane or triethylenetetramine, or other diamines, such as the aforementioned aliphatic or cycloaliphatic diamines;

adducts obtainable by reaction of amines, especially diamines, with a deficiency of epoxy resin, preference being given to using those adducts in which about 5% to 20% of the epoxy groups have been reacted with amines, especially diamines;

phenalkamines as known from epoxide chemistry;

Mannich bases which are prepared, for example, by condensation of polyamines, preferably diethylenetriamine, triethylenetetramine, isophoronediamine, 2,2,4- or 2,4,4-trimethylhexamethylenediamine, 1,3- and 1,4-bis(aminomethyl)cyclohexane, with aldehydes, preferably formaldehyde, and mono- or polyhydric phenols having at least one aldehyde-reactive core site, for example the various cresols and xylenols, p-tert-butylphenol, resorcinol, 4,4'-dihydroxydiphenylmethane, 4,4'-dihydroxydiphenyl-2,2-propane, but preferably phenol;

and mixtures of the aforementioned amine hardeners, especially mixtures of difunctional amines from the group of the aliphatic, cycloaliphatic and aromatic amines with the aforementioned polyetheramines.

Preferred aminic hardeners are aliphatic polyamines, especially 2,2-dimethylpropylenediamine, aromatic diamines, especially m-xylylenediamine (MXDA) and cycloaliphatic diamines, especially isophoronediamine, N-cyclohexylpropylene-1,3-diamine, Methyl cyclohexanediamine and 4,4'-diaminodicyclohexylmethane (Dicykan). Preference is also given to difunctional or trifunctional primary polyetheramines based on polypropylene glycol, for example Jeffamine® D 230 or Jeffamine® T 403. Particular preference is given to polyamines in which there is high mobility and low steric hindrance around the amino group, for example 4,9-dioxadodecane-1,12-diamine, 4,7,10-trioxatridecane-1,13-diamine, PolyTHF Amine 350 (BASF SE).

Preference is also given to mixtures of the amines specified as preferred, for example mixtures comprising 2,2-dimethyl-1,3-propanediamine and isophoronamine.

The compositions of the present invention may be used as a one component mixture with at least one latent hardener which is activatable by moisture, said hardener being selected from the group consisting of oxazolidines, aldimines, ketimines and enamines.

The alcoholic hardeners include particularly aliphatic and cycloaliphatic alcohols of low molecular weight and higher molecular weight. Alcoholic hardeners crosslink carbonate polymers by reaction of the primary or secondary alcohol functions with the 1,3-dioxolan-2-one groups of the carbonate polymers to form diesters of carbonic acid. Preferred alcoholic hardeners have an average of at least two primary or secondary hydroxyl groups per molecule, for example two, three or four primary or secondary hydroxyl groups per molecule. Suitable alcoholic hardeners of low molecular weight are, for example, butane-1,4-diol, ethylene glycol, diethylene glycol, triethylene glycol, neopentyl glycol, propane-1,3-diol, pentane-1,5-diol, hexane-1,6-diol, glycerol, diglycerol, pentaerythritol, dipentaerythritol, isosorbide, sugar alcohols such as sorbitol and mannitol.

Suitable alcoholic hardeners are also higher molecular weight polymeric polyols, for example polyester polyols, polycarbonate polyols, polyether polyols, polyacrylate polyols and polyvinyl alcohols. Suitable polymeric polyol hardeners preferably have a mean OH functionality of at least 1.5 mol and especially at least 1.8, for example in the range from 1.5 to 10 and especially in the range from 1.8 to 4. The mean OH functionality is understood to mean the mean number of OH groups per polymer chain. Typical polymeric polyol components preferably have a number-average molecular weight of about 250 to 50 000 g/mol, preferably of about 500 to 10 000 g/mol. Preferably, at least 50 mol % of the hydroxyl groups present in the polymeric polyol component are primary hydroxyl groups.

Preferably, polyester polyols are linear or branched polymeric compounds having ester groups in the polymer backbone and having free hydroxyl groups at the ends of the polymer chain. Preferably, these are polyesters which are obtained by polycondensation of dihydric alcohols with dibasic carboxylic acids, optionally in the presence of higher polyhydric alcohols (e.g. tri-, tetra-, penta- or hexahydric alcohols) and/or higher polybasic polycarboxylic acids. Rather than the free di- or polycarboxylic acids, it is also possible to use the corresponding di- or polycarboxylic anhydrides or corresponding di- or polycarboxylic esters of lower alcohols or mixtures thereof for preparation of the polyester polyols. The di- or polycarboxylic acids may be aliphatic, cycloaliphatic, araliphatic, aromatic or heterocyclic, preferably have 2 to 50 and especially 4 to 20 carbon atoms and may optionally be substituted, for example by halogen atoms, and/or be unsaturated. Examples thereof include: suberic acid, azelaic acid, phthalic acid, isophthalic acid, phthalic anhydride, tetrahydrophthalic anhydride, hexahydrophthalic anhydride, tetrachlorophthalic anhydride, endomethylenetetrahydrophthalic anhydride, glutaric anhydride, maleic acid, maleic anhydride, alkenylsuccinic acid, fumaric acid and dimeric fatty acids. Useful diols for the preparation of the polyester polyols include especially aliphatic and cycloaliphatic diols having preferably 2 to 40 and especially 2 to 20 carbon atoms, for example ethylene glycol, propane-1,2-diol, propane-1,3-diol, butane-1,3-diol, butane-1,4-diol, butene-1,4-diol, butyne-1,4-diol, pentane-1,5-diol, neopentyl glycol, bis(hydroxymethyl)cyclohexanes such as 1,4-bis(hydroxymethyl)cyclohexane, 2-methylpropane-1,3-diol, methylpentanediols, and also diethylene glycol, triethylene glycol, tetraethylene glycol, polyethylene glycol, dipropylene glycol, polypropylene glycol, dibutylene glycol and polybutylene glycols. Preference is given to alcohols of the general formula HO—$(CH_2)_x$—OH, where x is a number from 2 to 20, preferably an even number from 2 to 12. Examples thereof are ethylene glycol, butane-1,4-diol, hexane-1,6-diol, octane-1,8-diol and dodecane-1,12-diol. Additionally preferred are neopentyl glycol and pentane-1,5-diol.

Suitable alcoholic hardeners are also lactone-based polyester polyols, these being homo- or copolymers of lactones, preferably terminal hydroxyl-containing addition products of lactones onto suitable difunctional starter molecules. Useful lactones are preferably those which derive from compounds of the general formula HO—$(CH_2)_z$—COOH where z is a number from 1 to 20 and one hydrogen atom of one methylene unit may also be substituted by a $C_1$-$C_4$-alkyl radical. Examples are ε-caprolactone, β-propiolactone, γ-butyrolactone and/or methyl-ε-caprolactone and mixtures thereof. Suitable starter molecules are, for example, the low molecular weight dihydric alcohols mentioned above as a formation component for the polyester polyols. The corresponding polymers of ε-caprolactone are particularly preferred. It is also possible to use lower polyester diols or polyether diols as starters for preparation of the lactone polymers. Rather than the polymers of lactones, it is also possible to use the corresponding chemically equivalent polycondensates of the hydroxycarboxylic acids corresponding to the lactones.

Examples of suitable polyester polyols are, for example, the polyester polyols known from Ullmanns Enzyklopädie der Technischen Chemie, 4th Edition, Volume 19, pages 62 to 65.

In addition, polycarbonate polyols are also useful, as obtainable, for example, by reaction of phosgene with an excess of the low molecular weight alcohols mentioned as formation components for the polyester polyols.

The polyether polyols are especially polyether polyols preparable by polymerization of ethylene oxide, propylene oxide, butylene oxide, tetrahydrofuran, styrene oxide or epichlorohydrin with themselves, for example in the presence of $BF_3$ or by addition of these compounds, optionally in a mixture or in succession, onto bi- or polyfunctional starter components having reactive hydrogen atoms, such as polyols or polyfunctional amines, for example water, ethylene glycol, propane-1,2-diol, propane-1,3-diol, 1,1-bis(4-hydroxyphenyl)propane, trimethylolpropane, glycerol, sorbitol, ethanolamine or ethylenediamine. Also useful are sucrose polyethers (see DE 1176358 and DE 1064938), and formitol- or formose-started polyethers (see DE 2639083 and DE 2737951).

Likewise suitable are polyhydroxy olefins, preferably those having 2 terminal hydroxyl groups, e.g. α,ω-dihydroxypolybutadiene.

Likewise suitable are polyhydroxypolyacrylates, where the hydroxyl groups may be arranged laterally or terminally. Examples thereof are α,ω-dihydroxypoly(meth)acrylic esters obtainable by homo- or copolymerization of alkyl esters of acrylic acid and/or of methacrylic acid in the presence of regulators comprising OH groups, such as mercaptoethanol or mercaptopropanol, and subsequent transesterification with a low molecular weight polyol, for example an alkylene glycol such as butanediol. Such polymers are known, for example, from EP-A 622 378. Examples thereof are additionally polymers obtainable by copolymerization of alkyl esters of acrylic acid and/or of methacrylic acid with hydroxyalkyl esters of ethylenically unsaturated carboxylic acid such as hydroxyethyl acrylate, hydroxypropyl acrylate, hydroxybutyl acrylate, hydroxyethyl methacrylate, hydroxypropyl methacrylate or hydroxybutyl methacrylate.

Also suitable are polyvinyl alcohols, which can preferably be obtained by full or partial hydrolysis of polyvinyl esters, especially polyvinyl acetate. If the polyvinyl esters, preferably polyvinyl acetate, are in partly hydrolyzed form, preferably not more than 50% to 95% of the ester groups are in hydrolyzed form as hydroxyl groups. If the polyvinyl esters, preferably polyvinyl acetate, are in fully hydrolyzed form, generally more than 95% up to 100% of the ester groups are in hydrolyzed form as hydroxyl groups.

Alcoholic hardeners preferred among the higher molecular weight polymeric polyols are especially polyacrylate polyols, these being obtainable, for example, under the Joncryl® brand name from BASF SE, e.g. Joncryl® 945.

Suitable hardeners are also amino acids, for example lysine, arginine, glutamine and asparagine, and the stereoisomers thereof and mixtures thereof.

It will be appreciated that it is also possible to use mixtures of different hardeners, for example mixtures of one or more aminic hardeners with one or more alcoholic hardeners, mixtures of one or more aminic hardeners with one or more amino acids, or mixtures of one or more alcoholic hardeners with one or more amino acids.

In the binder compositions of the invention, the total amount of hardeners is preferably 0.1% by weight to 50% by weight, frequently 0.5% to 40% by weight and especially 1% to 30% by weight, based on the total amount of carbonate polymers plus hardeners used.

The binder composition can be hardened thermally by heating the mixture of polymer of the invention and hardener to a temperature above the mixing temperature. The hardening can also be effected at lower temperatures. Typically, the binder compositions of the invention are hardened at temperatures in the range from 0 to 200° C., preferably in the range from 5 to 180° C. and especially in the range from 10 to 150° C. The temperature which is suitable depends on the respective hardeners and the desired hardening rate, and can be determined in the individual case by the person skilled in the art, for example by simple preliminary tests. In the lower temperature range (5 to approx. 35° C.), which of course corresponds to the usually prevailing ambient temperature, it is of course sufficient to mix polymer of the invention and hardener. Alternatively, the hardening is preferably microwave-induced.

The two-pack binder compositions may also comprise one or more suitable catalysts for the hardening, which are guided in a known manner by the nature of the reactive functional groups F. The catalysts are, if desired, used in proportions of 0.01% by weight to about 10% by weight, based on the total weight of the polymers of the invention having functional alkylidene-1,3-dioxolan-2-one groups of the formula I and of the hardener. In one configuration, no catalysts are required, particularly in the case of hardeners which have amino groups as functional groups, which means that the content of catalysts in the composition in that case is less than 0.01% by weight. Catalysts are used with preference when the hardener has reactive groups F other than amino groups, especially when the hardener has hydroxyl groups.

Catalysts used with preference are basic catalysts, more preferably organic amines and organic phosphines. Among the organic amines, preference is given to amidine bases, for example 1,8-diazabicyclo[5.4.0]undec-7-ene (DBU) and 1,5-diazabicyclo[4.3.0]non-5-ene (DBN), and to mono-$C_1$-$C_6$-alkyl-, di-$C_1$-$C_6$-alkyl- and tri-$C_1$-$C_6$-alkylamines, especially triethylamine and tert-butylamine. Among the organic phosphines, preference is given to trialkylphosphines and tri-arylphosphines, for example tri-n-butylphosphine and triphenylphosphine. The catalysts can of course also be used as mixtures, optionally in combination with tri-$C_1$-$C_6$-alkylammonium halides and copper salts, for example triphenylphosphine in combination with a tri-$C_1$-$C_6$-alkyl-ammonium halide and a copper salt, e.g. copper(I) chloride, copper(I) bromide, copper(II) chloride or copper(II) sulfate. Guanidine, phenolate, benzoate As well as the aforementioned constituents, the two-pack binder composition may comprise the additives customary therefor. The choice of suitable conventional additives for the composition of the invention depends on the particular end use of the two-pack binder composition and can be determined in the individual case by the person skilled in the art.

Suitable additives comprise, for example, antioxidants, UV absorbers/light stabilizers, metal deactivators, antistats, reinforcers, fillers, antifogging agents, blowing agents, biocides, plasticizers, lubricants, emulsifiers, colorants, pigments, rheology agents, impact tougheners, adhesion regulators, optical brighteners, flame retardants, antidripping agents, nucleating agents, wetting agents, thickeners, protective colloids, defoamers, tackifiers, solvents and reactive diluents, and mixtures thereof.

Fillers may be organic and inorganic in nature; preferred inorganic fillers take the form of platelets which can be aligned to form layers having enhanced barrier action against liquids and gases. Examples are sheet silicates such as montmorillonite and hectorite, as described, for example, in WO 2011/089089, WO 2012/175427 or in WO 2012/175431. Preference is given to sheet silicates having an aspect ratio of at least 50, at least 400, or at least 1000, and especially greater than or equal to 10 000. The layer thickness is, for example, about 1 nm. The sheet silicates may be of natural or synthetic origin. Suitable sheet silicates are, for example, montmorillonite, bentonite, kaolinite, mica, hectorite, fluorohectorite, saponite, beidellite, nontronite, stevensite, vermiculite, fluorovermiculite, halloysite, volkonskoite, suconite, magadite, sauconite, stibensite, stipulgite, attapulgite, illite, kenyaite, smectite, allevardite, muscovite, palygorskite, sepiolite, silinaite, grumantite, revdite, zeolite, fuller's earth, natural or synthetic talc or mica, or permutite. Particular preference is given to montmorillonite (aluminum magnesium silicate), hectorite (magnesium lithium silicate), synthetic fluorohectorite and exfoliated, organically modified smectites. The sheet silicates may be modified or unmodified. Preference is given to cationically modified sheet silicates. "Cationically modified" means that inorganic cations in the sheet silicate have been at least partly exchanged for organic cations, for example by an ion exchange method. Organic cations are organic compounds having at least one cationic group, for example quaternary ammonium group, phosphonium group, pyridinium group or the like, or a cationic amine salt.

Any light stabilizers/UV absorbers, antioxidants and metal deactivators used preferably have a high migration stability and thermal stability. They are selected, for example, from groups a) to t). The compounds of groups a) to g) and i) are light stabilizers/UV absorbers, while compounds j) to t) act as stabilizers.
a) 4,4-diarylbutadienes,
b) cinnamic esters,
c) benzotriazoles,
d) hydroxybenzophenones,
e) diphenyl cyanoacrylates,
f) oxamides,
g) 2-phenyl-1,3,5-triazines,
h) antioxidants,
i) nickel compounds,
j) sterically hindered amines,
k) metal deactivators,
l) phosphites and phosphonites,
m) hydroxylamines,
n) nitrones,
o) amine oxides,
p) benzofuranones and indolinones,
q) thio synergists,
r) peroxide-destroying compounds,
s) polyamide stabilizers and
t) basic costabilizers.

The two-pack adhesive is preferably free of isocyanates, meaning that it is preferably does not comprise any isocyanate compounds as hardeners. The two-pack adhesive is preferably either in the form of a solution in an organic solvent or is solvent-free. "Solvent-free" means that less than 5% by weight, more preferably less than 2% by weight or zero organic solvent or water is present.

The inventive two-component composition usually develops high binding strength in a short time, in particular with amine hardeners, already at room temperature.

The inventive two-component composition can be applied as adhesive in laminating processes such as described in detail in WO 2017/207461 A1, on pages 20 to 25.

The inventive two-component composition can also be applied for bonding of solid substrates as wood, metals various plastics, composites, paper, cardboard, fiber reinforced materials, concrete or various mineral building materials.

The inventive compounds of formula (I) can be used in combination with polyfunctional amines or polyols as a component of coating material compositions for the coating of metallic or non-metallic surfaces such as described in WO 2015/039807.

The inventive compounds of formula (I) together with an appropriate hardener as described above forms polymers, which fulfil the intended application. Alternatively, the inventive compounds of formula (I), wherein m is 1 or 2 can be also polymerized alone or together with suitable further monomers comprising at least one polymerizable carboncarbon double bonds to form polymers, that means homo- or copolymers.

Therefore, a further aspect of the present invention is a polymer formed from one or more monomers, wherein at least one monomer is a compound of formula (I) as described above.

In one embodiment of the present invention, the inventive polymer is characterized in that the polymer is a reaction product of the compound of formula (I) as described above and one or more compounds which comprise at least two functional groups selected from the group consisting of primary amino groups, secondary amino groups, hydroxy groups, carboxylate groups, phosphine groups, phosphonate groups and mercaptan groups, preferably selected from polyols, polyacids, polyamines, polyamido-amines and mixtures thereof.

A further aspect of the present invention is a two-component composition comprising as a first component a polymer as described above and as a second component at least one multifunctional hardener that comprises at least two functional groups selected from the group consisting of primary amino groups, secondary amino groups, hydroxy groups, phosphine groups, phosphonate groups and mercaptan groups.

A further aspect of the present invention is the use of the compound of formula (I), of the two-component composition as described above or of the polymer as described above as a component of an adhesive and/or sealant for rigid and flexible parts, made from metal, plastic, paper, paperboard, textiles, glass, leather, wood and inorganic materials.

A further aspect of the present invention is the use of the compound of formula (I), of the two-component composition as described above or of the polymer as described above as a component of a coating for rigid and flexible substrates, made from metal, plastic, paper, paperboard, textiles, glass, leather, wood and inorganic materials.

A further aspect of the present invention is the use of the compound of formula (I), of the two-component composition as described above or of the polymer as described above as a component of a binder for fibers, particles and pigments.

A further aspect of the present invention is the use of the compound of formula (I), of the two-component composition as described above or of the polymer as described above as a component of foam rubbers, preferably together with an appropriate foaming agent.

A further aspect of the present invention is the use of any compound as described above, that means the compound of formula (I), the polymers obtainable by polymerizing the compound of formula (I) alone or together with additional monomers and the above described two-component compositions, as an intermediate for the preparation of polyunsaturated compounds by reacting a (oligo/poly)-functional nucleophile with a compound of formula (I). The obtained reaction product can be subsequently applied to further curing (e.g. radical induced curing).

The invention is illustrated by the examples which follow, but these do not restrict the invention.

Figures in percent are each based on % by weight, unless explicitly stated otherwise.

General

All chemicals and solvents were purchased from Sigma-Aldrich or ABCR and used without further purification.

$^1$H and $^{13}$C NMR spectra were recorded on Bruker Avance 200 MHz and 400 MHz spectrometer and were referenced to the residual proton ($^1$H) or carbon ($^{13}$C) resonance peaks of the solvent.

Chemical shifts ($\delta$) are reported in ppm.

Used abbreviations: Davephos-Ligand A=2-Dicyclohexylphosphino-2'-(N,N-dimethylamino)biphenyl; DCM=Dichloromethane; DIPEA=N,N-Diisopropylethylamine; DMAP=4-Dimethylaminopyridine; DMF=Dimethylformamide; PE=Petroleum ether; THF=Tetrahydrofuran; TMEDA=Tetramethylethylenediamine;

I. Synthesis of the Starting Materials and of Compounds of Formula (II)

I.1 4-hydroxybut-2-yn-1-yl methacrylate

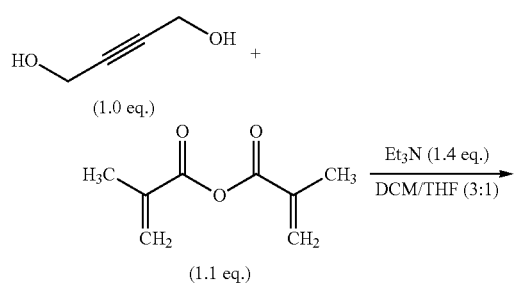

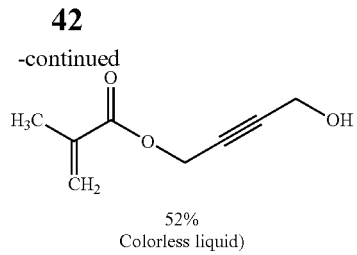

52%
Colorless liquid)

Distilled Et$_3$N (5.6 mL, 40.6 mmol, 1.4 eq.) was added to a solution of but-2-yne-1,4-diol (2.5 g, 29.0 mmol, 1.0 eq.) in dry DCM/THF (12 mL/4 mL), and the resulting suspension was stirred at room temperature until dissolution was complete. Methacrylic anhydride (4.75 mL, 31.9 mmol, 1.1 eq.) was then added to the reaction mixture at 0° C. dropwise over 30 min. The reaction mixture was then warmed to room temperature and stirred overnight. Water was added and the reaction mixture was extracted with DCM (3022×2 mL). The collected organic layers were dried and the solvents were evaporated in vacuo. Flash chromatography of the crude products (silica gel, EtOAc/PE 2:3) gave the pure product as a colourless oil (2.3 g, 52%).

$^1$H NMR (400 MHz, CDCl$_3$): $\delta$=6.12-6.13 (m, 1H), 5.60-5.58 (s, 1H), 4.76-4.75 (m, 2H), 4.28-4.27 (m, 2H), 2.61 (br.s, 1H), 1.93-1.92 (m, 3H). $^{13}$C NMR (101 MHz, CDCl$_3$): $\delta$=166.9, 135.7, 126.7, 85.2, 79.7, 52.6, 50.9, 18.3. HRMS (ESI, 70 eV): m/z calcd. for C$_8$H$_{10}$O$_3$: 154.0625 [M+]; found: 154.0618.

I.2 2-((((4-hydroxybut-2-yn-1-yl)oxy)carbonyl)amino)ethyl methacrylate

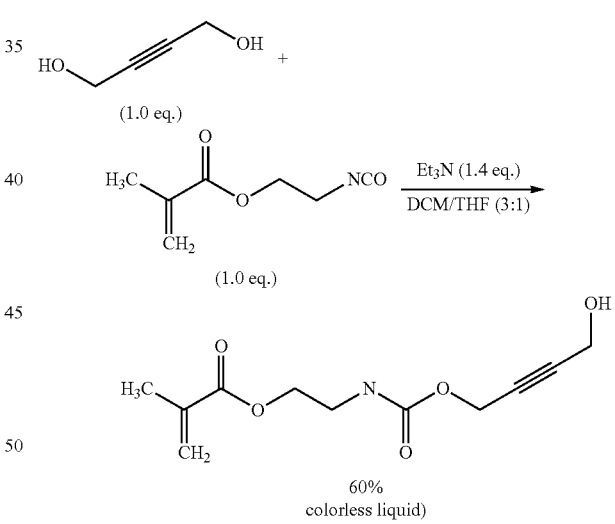

60%
colorless liquid)

Distilled Et$_3$N (8.9 mL, 63.8 mmol, 1.1 eq.) was added to a solution of but-2-yne-1,4-diol (5.0 g, 58.0 mmol, 1.0 eq.) in dry DCM/THF (24 mL/8 mL), and the resulting suspension was stirred at room temperature until dissolution was complete. 2-isocyanatoethyl methacrylate (8.6 mL, 58.0 mmol, 1.0 eq.) was then added to the reaction mixture at 0° C. dropwise over 30 min. The reaction mixture was then warmed to room temperature and stirred overnight. Water was added and the reaction mixture was extracted with DCM (3044×4 mL). The collected organic layers were dried and the solvents were evaporated in vacuo. Flash chromatography of the crude (silica gel, EtOAc/PE 7:3) gave the pure product (R$_f$=0.35) as a colourless oil (8.4 g, 60%)

¹H NMR (400 MHz, CDCl₃): δ=6.13-6.12 (m, 1H), 5.61-5.60 (s, 1H), 5.06 (br.s, 1H), 4.73 (s, 2 H), 4.31-4.30 (m, 2H), 4.26-4.23 (m, 2H), 3.54-3.50 (m, 2H), 1.95 (s, 3H), 1.73 (br.s, 1H). ¹³C NMR (101 MHz, CDCl₃): δ=167.2, 155.5, 135.9, 126.1, 84.9, 80.2, 63.6, 52.9, 51.1, 40.4, 18.3.

I.3 4,4'-((1,4-phenylenebis(methylene))bis(oxy))bis(but-2-yn-1-ol)

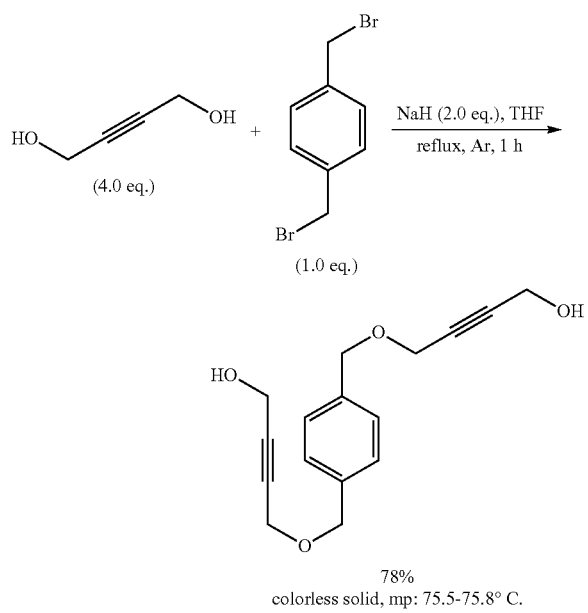

78%
colorless solid, mp: 75.5-75.8° C.

But-2-yne-1,4-diol (2.6 g, 30.2 mmol, 4.0 eq.) dissolved in anhydrous THF (10 mL) was added dropwise into a 100 mL three-neck round bottom flask containing a solution of NaH (0.37 g, 15.2 mmol, 2.0 eq.) in anhydrous THF (12 mL). After stirring for 30 min, 1,4-bis(bromomethyl) benzene (2.0 g, 7.58 mmol, 1.0 eq.) was added and the mixture was refluxed overnight. The solvent was removed in vacuo and the residue was purified by column chromatography (silica gel, EtOAc/PE 7:3) to afford the desired product as white solid (1.62 g, 78%).

¹H NMR (400 MHz, CDCl₃): δ=7.35-7.27 (m, 4H), 4.60 (s, 4H), 4.33 (br.s, 4H), 4.22-4.20 (m, 4H), 1.99 (br.s, 2H). ¹³C NMR (101 MHz, CDCl₃): δ=137.2 (2C), 128.4 (4C), 84.9 (2C), 81.9 (2C), 71.6 (2C), 57.6 (2C), 51.3 (2C). IR (KBr): 3279, 3201, 2914, 1402, 1368, 1342, 1236, 1138, 1069, 1007, 989, 839, 759, 585, 537. HRMS (EI): m/z calcd. for C₁₆H₁₈O₄: 274.1176 [M⁺]; found: 274.1199.

I.4 bis(4-hydroxybut-2-yn-1-yl)(4-methyl-1,3-phenylene) dicarbamate

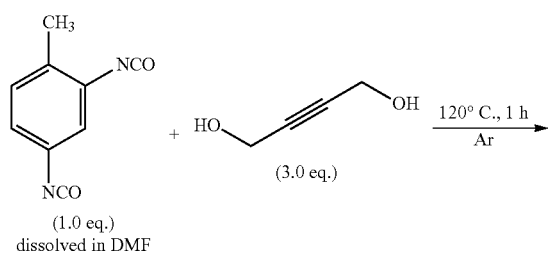

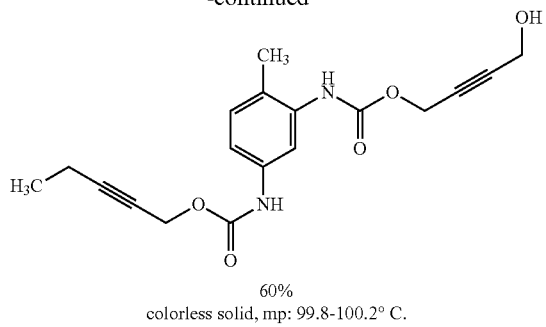

60%
colorless solid, mp: 99.8-100.2° C.

2,4-diisocyanato-1-methylbenzene (1.0 g, 5.8 mmol, 1.0 eq.) dissolved in anhydrous DMF (5.0 mL) was added dropwise (2 drop/sec) into an argon purged 100 mL three-neck round bottom flask containing but-2-yne-1,4-diol (1.5 g, 17.4 mmol, 3.0 eq.) at 120° C. After the addition was complete, the reaction mixture was further stirred for 1 h at 120° C. after which it was brought down to room temperature. Distilled water (90 mL) was then added to the above reaction mixture and the product was let to crystallize in the freezer overnight. The crystals were filtered and recollected in a 250 mL round bottom flask containing 150 mL water. The mixture was then refluxed at 110° C., followed by hot filtration. The oligomers were separated by filtration while the filtrate at the bottom was cooled down to obtain the product as a white solid (1.2 g, 60%). ¹H NMR (400 MHz, CD₃CN): δ=7.79 (br.s,1H), 7.73 (br.s, 1H), 7.21 (s, 1H), 7.18-7.15 (m, 1H), 7.13-7.11 (m, 1H), 4.78-4.75 (m, 4H), 4.21-4.18 (m, 4H), 3.18-3.14 (m, 2H), 2.18 (s, 3H). ¹³C NMR (101 MHz, CD₃CN): δ=154.4, 153.9, 137.8, 137.2, 131.6, 126.0, 116.2, 114.4, 86.5 (2C), 80.0 (2C), 53.6 (2C), 53.4, 50.6, 17.3. IR (KBr): 3292, 1704, 1605, 1539, 1498, 1451, 1429, 1318, 1283, 1235, 1185, 1144, 1060, 1015, 882, 817, 762. HRMS (ESI): m/z calcd. for C₁₇H₁₈N₂O₆: 369.106 [M+Na⁺]; found: 369.106.

I.5 1,8-Bis(4-hydroxy-2-butyn-1-oxy)-3,6-dioxaoctane

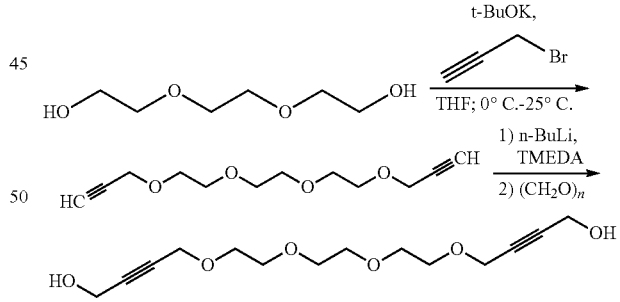

The diol was synthesized in two steps.

I.5.a Synthesis of 4,7,10,13-tetraoxahexadeca-1,15-diyne

In an argon flushed 100 mL three-neck round bottom flask was charged a solution of 2,2'-(ethane-1,2-diylbis(oxy))bis (ethan-1-ol) (2.13 g, 14.2 mmol, 1 eq.) in THF (5.0 mL) to a cooled (0° C.) suspension of t-BuOK (3.77 g, 32.0 mmol, 2.3 eq.) in 30 mL of THF. The resulting reaction mixture was allowed to warm to room temperature and was then added dropwise to an ice cooled solution (0° C.) of propargyl bromide (6.3 mL, 56.5 mmol, 4.0 eq.) in 120 mL of THF, under argon atmosphere. The reaction mixture was stirred for an additional 18 h and the reaction let to warm to room temperature. A 3:1 brine/water (75 mL) solution was then added to the above mixture and the aqueous layer was extracted with EtOAc (35050×50 mL) followed by drying in vacuo. The residue was purified by flash chromatography on silica gel (EtOAc/PE 1:1) to afford bis(propargyl ether) (2.24 g, 70%) as yellow oil.

I.5.b Synthesis of 1,8-Bis(4-hydroxy-2-butyn-1-oxy)-3,6-dioxaoctane

In an argon-flushed 250 mL three-neck round bottom flask was added a solution of bis(propargyl) ether (2.5 g, 10.9 mmol, 1 eq.) in 91 mL of THF and TMEDA (16.7 mL, 11.8 mmol, 10 eq.). The mixture was then cooled to −78° C., followed by the drop-wise addition of n-BuLi (16.0 mL, 1.6 M solution, 26.6 mmol, 2.4 eq.). After an additional 5 min stirring, a suspension of paraformaldehyde (7.2 g, 22 mmol) in 7 mL of THF under argon was added via syringe. The reaction mixture was slowly allowed to warm to room temperature and stirred for an additional 1 h before diluting with 150 mL of saturated aqueous $NaH_2PO_4$. The aqueous layer was extracted with EtOAc (6033×3 mL), and the combined organic layers were washed with 120 mL of saturated $NaHCO_3$ and 120 mL of brine. The residue upon drying and concentration was purified by flash chromatography (EtOAc/MeOH 98:2) to afford the diol ($R_f$ 0.35) as a pale yellow solid (1.3 g, 42%).

$^1H$ NMR (400 MHz, $CDCl_3$): δ=4.25-4.24 (m, 4H), 4.20-4.19 (m, 4H), 3.67-3.63 (m, 12H), 3.05 (br.s, 2H). $^{13}C$ NMR (101 MHz, $CDCl_3$): δ=85.2 (2C), 81.3 (2C), 70.6 (2C), 70.5 (2C), 69.1 (2C), 58.7 (2C), 50.7 (2C). HRMS (ESI, 70 eV): m/z calcd. for $C_{14}H_{22}O_6$: 309.131 [M+Na$^+$]; found: 309.131.

II. Synthesis of the Starting Materials and of Compounds of Formula (I)

General Reaction Procedure

A steel autoclave was charged with Alkynol, in particular compounds of general formula (II) (5.0 mmol), AgOAc (1 or 2 mol %), and Davephos-Ligand A (1 or 2 mol %) and MeCN (10 mL). The reaction mixture was pressurized with $CO_2$ (20 bar) and stirred at room temperature for 18 h. Then $CO_2$ overpressure was carefully released and solvent evaporated. The resulting crude mixture was purified by flash column chromatography (silica gel, EtOAc/PE gradient).

Isolated Products

II.1 (Z)-4-(2-hydroxyethylidene)-1,3-dioxolan-2-one

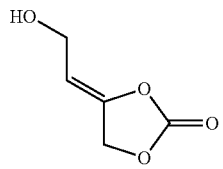

Colorless oil, yield: 0.45 g (65%). $^1H$ NMR (200 MHz, $CDCl_3$): δ=4.97-4.88 (m, 3H), 4.18-4.15 (m, 2H), 3.33 (s, 1H). $^{13}C$ NMR (50 MHz, $CDCl_3$): δ=152.9, 143.2, 102.4, 67.6, 55.7. HRMS (EI): m/z calcd. for $C_5H_6O_4$: 130.0260 [M$^+$]; found: 130.0259.

II.2 (Z)-2-(2-oxo-1,3-dioxolan-4-ylidene)ethyl methacrylate

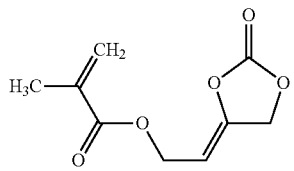

White solid, yield: 0.81 g (82%). mp: 36.1-36.3° C. $^1H$ NMR (400 MHz, $CDCl_3$) δ=6.12-6.11 (m, 1H), 5.59-5.58 (m, 1H), 5.02-4.99 (m, 3H), 4.80-4.78 (m, 2H), 1.94 (s, 3H). $^{13}C$ NMR (101 MHz, $CDCl_3$) δ=167.2, 152.1, 145.4, 136.1, 126.2, 98.1, 67.4, 58.0, 18.4. IR (KBr): 3402, 2933, 2356, 216.9, 1818, 1707, 1723, 1632, 1534, 1455, 1400, 1383, 1326, 1288, 1229, 1156, 1133, 1088, 1045, 1011, 971, 920, 868, 841, 817, 766, 732, 645, 617, 571. HRMS (EI): m/z calcd. for $C_9H_{10}O_5$: 198.0523 [M$^+$]; found: 198.0519. Anal. Calcd. for $C_9H_{10}O_5$: C 54.55%, H 5.09%, Found: C 54.77%, H 5.13%.

II.3 (Z)-2-(((2-(2-oxo-1,3-dioxolan-4-ylidene)ethoxy)carbonyl)amino)ethyl methacrylate

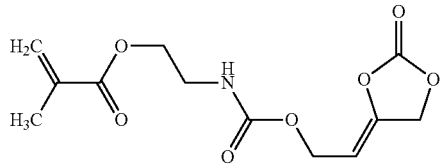 [SMILES: C=C(C)C(=O)OCCNC(=O)OC/C=C1/COC(=O)O1]

White solid, yield: 1.34 g (94%). mp: 86.5-86.7° C. $^1H$ NMR (400 MHz, $CDCl_3$) δ=6.12-6.11 (m, 1H), 5.59-5.57 (m, 1H), 5.00-4.97 (m, 3H), 4.71-4.69 (m, 2H), 4.24-4.21 (m, 2H), 3.51-3.47 (m, 2H), 1.94 (s, 3H). $^{13}C$ NMR (101 MHz, $CDCl_3$) δ=167.4, 156.2, 152.1, 145.2, 136.1, 126.2, 98.6, 67.4, 63.7, 58.3, 40.4, 18.4. IR (KBr): 3360, 3060, 1826, 1726, 1690, 1632, 1539, 1471, 1437, 1385, 1327, 1306, 1253, 1217, 1139, 1046, 1012, 967, 936, 873, 805, 760, 736, 621, 557. HRMS (ESI): m/z calcd. for $C_{12}H_{15}NO_7$: 308.074 [M+Na$^+$]; found: 308.074. Anal. Calcd. for $C_{12}H_{15}NO_7$: C 50.53%, H 5.30%, N 4.91%, Found: C 50.24%, H 5.06%, N 5.06%.

II.4 (4Z,4'Z)-4,4'-(((1,4-phenylenebis(methylene))bis(oxy))bis(ethan-2-yl-1-ylidene))bis(1,3-dioxolan-2-one)

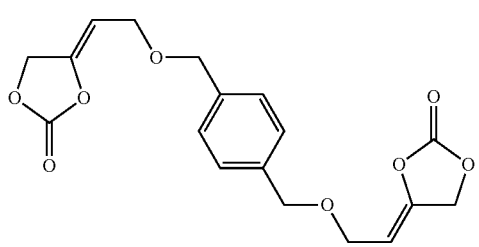 [SMILES: O=C1OC/C(=C/COCc2ccc(COC/C=C3/COC(=O)O3)cc2)O1]

White solid, yield: 1.56 g (86%). mp: 108.6-109.0° C. $^1H$ NMR (400 MHz, $CDCl_3$) δ=7.33-7.26 (m, 4H), 5.00-4.93 (m, 6H), 4.52 (m, 4H), 4.21-4.16 (m, 4H). $^{13}C$ NMR (101 MHz, $CDCl_3$) δ=152.2 (2C), 144.0 (2C), 137.4 (2C), 128.0 (4C), 100.3 (2C), 72.5 (2C), 67.3 (2C), 63.3 (2C). IR (KBr): 2855, 1833, 1702, 1461, 1385, 1295, 1212, 1134, 1085, 1055, 1035, 976, 905, 835, 821, 763. HRMS (ESI): m/z calcd. for $C_{18}H_{18}O_8$: 363.107 [M+H$^+$]; found: 363.107. Anal. Calcd. for $C_{18}H_{18}O_8$: C 59.67%, H 5.01%, Found: C 59.54%, H 4.76%.

II.5 bis((Z)-2-(2-oxo-1,3-dioxolan-4-ylidene)ethyl)(4-methyl-1,3-phenylene)dicarbamate

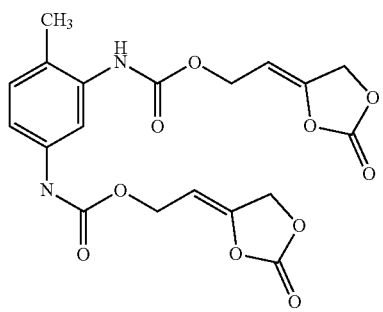 [SMILES: Cc1ccc(NC(=O)OC/C=C2/COC(=O)O2)cc1NC(=O)OC/C=C1/COC(=O)O1]

White solid, yield: 2.02 g (93%). mp: 175.5-176.1° C. $^1$H NMR (400 MHz, CD$_3$CN) δ=7.75-7.70 (m, 2H), 7.12-7.11 (m, 3H), 5.05-5.00 (m, 6H), 4.76-4.69 (m, 4H), 2.15 (s, 3H).

II.6 (4Z,4'Z)-4,4'-(3,6,9,12-tetraoxatetradecane-1,14-diylidene)bis(1,3-dioxolan-2-one)

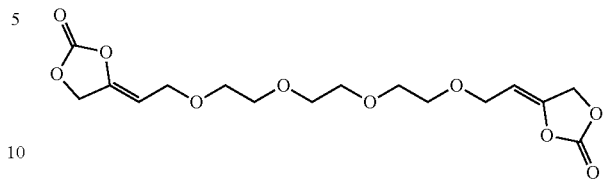

Colorless oil, yield: 1.78 g (95%). $^1$H NMR (400 MHz, CDCl$_3$) δ=5.00-4.90 (m, 6H), 4.20-4.15 (m, 4H), 3.65-3.58 (m, 12H). $^{13}$C NMR (101 MHz, CDCl$_3$) δ=152.4 (2C), 144.1 (2C), 100.4 (2C), 70.8 (2C), 70.7 (2C), 69.9 (2C), 67.5 (2C), 64.3 (2C). IR (KBr): 2872, 1833, 1723, 1464, 1381, 1297, 1214, 1131, 1106, 1046, 949, 870, 765, 733. HRMS (ESI): m/z calcd. for $C_{16}H_{22}O_{10}$: 397.110 [M+Na$^+$]; found: 397.110. Anal. Calcd. for $C_{16}H_{22}O_{10}$: C 51.34%, H 5.92%, Found: C 51.48%, H 6.00%.

III. 5,9,14,18-tetraoxadocosa-2,20-diyne-1,7,16,22-tetraol

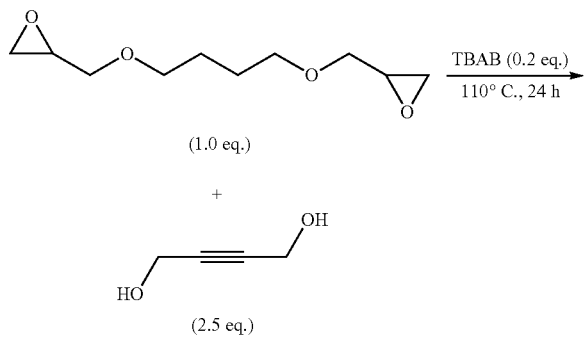

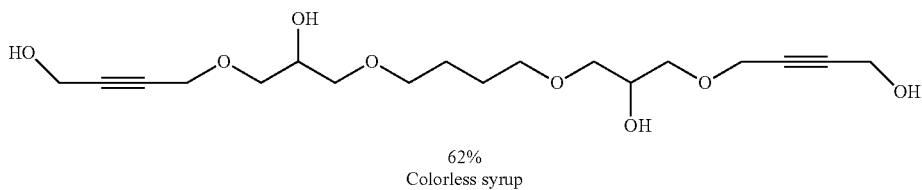

62%
Colorless syrup $^{13}$C NMR (101 MHz, CD$_3$CN) δ=154.9, 154.4, 153.7, 147.3 (2C), 138.1, 137.4, 131.6 (2C), 125.7, 116.1, 114.4, 98.2 (2C), 68.9 (2C), 59.2, 59.0, 17.3. IR (KBr): 3360, 1830, 1723, 1606, 1542, 1457, 1387, 1284, 1224, 1179, 1130, 1098, 1042, 874, 815, 764, 730, 566. HRMS (ESI): m/z calcd. for $C_{19}H_{18}N_2O_{10}$: 457.086 [M+Na$^+$]; found: 457.085. Anal. Calcd. for $C_{19}H_{18}N_2O_{10}$: C 52.54%, H 4.18%, N 6.45%, Found: C 52.62%, H 4.22%, N 6.55%.

But-2-yne-1,4-diol (1.70 g, 19.75 mmol, 2.5 eq.) and tetrabutylammonium bromide (TBAB, 0.50 g, 1.58 mmol, 0.2 eq.) were taken in an Argon flushed 50 mL three neck round bottom flask. To this, was added 12 mL chlorobenzene and the mixture was heated to 110° C. until the reagents were completely dissolved. A solution of 1,4-butanediol diglycidyl ether (1.60 g, 7.91 mmol, 1.0 eq.) in 10 mL chlorobenzene was then added to the above mixture with the help of a syringe and the reaction was heated overnight. Flash chromatography of the crude (silica gel, EtOAc/MeOH=96:4) gave the pure product ($R_f$=0.22 in EtOAc/MeOH=96:4) as a colourless oil (1.84 g, 62%).

$^1$H NMR (300 MHz, CD$_3$CN): δ=4.18 (s, 8H), 3.82 (br.s, 2H), 3.51 (dd, J=9.9 Hz, 4.4 Hz, 2H), 3.46-3.32 (m, 12H), 3.17 (br.s, 2H), 1.61-1.57 (m, 4H). $^{13}$C NMR (75 MHz, CD$_3$CN): δ=86.3 (2C), 81.5 (2C), 72.9 (2C), 72.2 (2C), 71.8 (2C), 70.1 (2C), 59.3(2C), 50.6(2C), 27.1 (2C). IR (film): v=3392, 2919, 2867, 1445, 1356, 1229, 1122, 1090, 1016, 873, 597 cm$^{-1}$. HRMS (ESI): m/z calcd. for C$_{18}$H$_{30}$O$_8$: 397.1833 [M+Na$^+$]; found: 397.1832.

4,4'-((((propane-2,2-diylbis(4,1-phenylene))bis(oxy))bis(2-hydroxypropane-3,1-diyl))bis(oxy))bis(but-2-yn-1-ol)

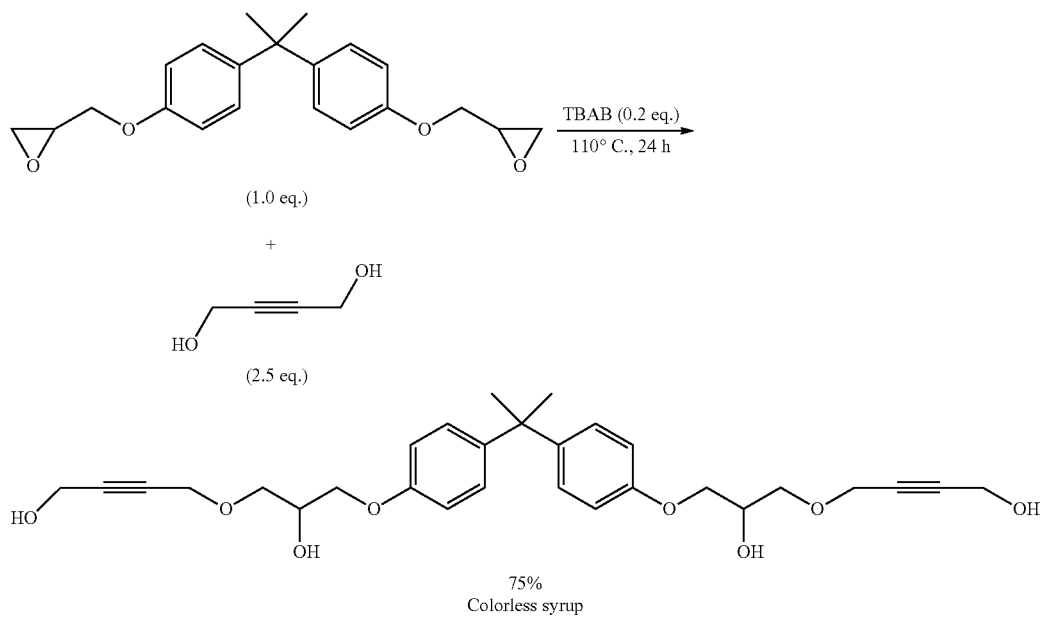

75%
Colorless syrup

But-2-yne-1,4-diol (2.15 g, 24.96 mmol, 2.5 eq.) and tetrabutylammonium bromide (TBAB, 0.65 g, 1.99 mmol, 0.2 eq.) were taken in an Argon flushed 50 mL three neck round bottom flask. To this, was added 15 mL chlorobenzene and the mixture was heated to 110° C. until the reagents were completely dissolved. A solution of bisphenol-A-diglycidyl ether (3.40 g, 9.98 mmol, 1.0 eq.) in 15 mL chlorobenzene was then added to the above mixture with the help of a syringe and the reaction was heated overnight. Flash chromatography of the crude (silica gel, EtOAc/MeOH=98:2) gave the pure product ($R_f$=0.54 in EtOAc/MeOH=98:2) as a colourless oil (3.84 g, 75%).

$^1$H NMR (400 MHz, CD$_3$CN): δ=7.14 (d, J=8.8 Hz, 4H), 6.83 (d, J=8.8 Hz, 4H), 4.18 (m, 8H), 3.99 (dd, J=18.8 Hz, 13.4 Hz, 4H), 3.90 (dd, J=9.7 Hz, 6.0 Hz, 2H), 3.58 (ddd, J=15.7 Hz, 9.9 Hz, 5.2 Hz, 4H), 3.27 (d, J=4.9 Hz, 2H), 3.16 (t, J=5.8 Hz, 2H), 1.61 (s, 6H). $^{13}$C NMR (101 MHz, CD$_3$CN): δ=157.7 (2C), 144.3 (2C), 128.6 (4C), 114.9 (4C), 86.4 (2C), 81.4 (2C), 71.8 (2C), 70.3 (2C), 69.7 (2C), 59.3 (2C), 50.6 (2C), 42.3, 31.2 (2C). IR (film): v=3379, 2931, 2871, 1607, 1510, 1461, 1361, 1297, 1248, 1184, 1124, 1087, 1013, 830, 575 cm$^{-1}$. HRMS (ESI): m/z calcd. for C$_{29}$H$_{36}$NaO$_8$: 535.2305 [M+Na$^+$]; found: 535.2302.

General Procedure for the Carboxylative Cyclisation of 1,4-butynediol Derivatives A steel autoclave was charged with Alkynol (5.0 mmol), AgOAc (5 mol %), Ligand A (5 mol %) and solvent (10 mL) under atmospheric conditions. The reaction mixture was pressurized with CO$_2$ (20 bar) and stirred at room temperature for 18 h. Then CO$_2$ overpressure was carefully released and solvent evaporated. The resulting crude mixture was purified by flash column chromatograph.

(4Z,4'Z)-4,4'-(((((propane-2,2-diylbis(4,1-phenylene))bis(oxy))bis(2-hydroxy propane-3,1-diyl))bis(oxy))bis(ethan-2-yl-1-ylidene))bis(1,3-dioxolan-2-one)

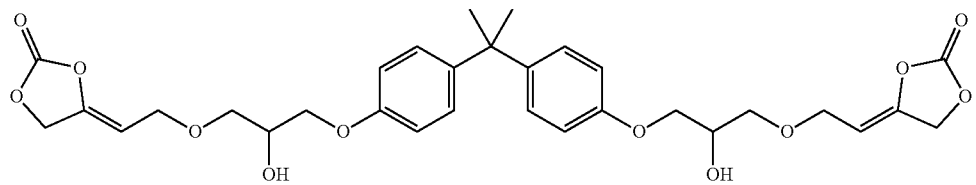 [SMILES: CC(C)(c1ccc(OCC(O)COC/C=C2/COC(=O)O2)cc1)c1ccc(OCC(O)COC/C=C2/COC(=O)O2)cc1]

Colorless oil, 545 mg (93%) for a reaction scale of 0.97 mmol. $R_f$ (EtOAc)=0.59. $^1$H NMR (300 MHz, CDCl$_3$): δ=7.16-7.10 (m, 4H), 6.84-6.78 (m, 4H), 5.01-4.88 (m, 6H), 4.23-4.21 (m, 2H), 4.20-4.18 (m, 2H), 4.17-4.09 (m, 2H), 4.03-3.95 (m, 4H), 3.67-3.56 (m, 4H), 2.52 (br.s, 2H), 1.63 (s, 6H). $^{13}$C NMR (75 MHz, CDCl$_3$): δ=156.4 (2C), 152.3

(2C), 144.4 (2C), 143.8 (2C), 127.9 (4C), 114.0 (4C), 99.9 (2C), 71.3 (2C), 69.2 (2C), 68.9 (2C), 67.4 (2C), 64.5 (2C), 41.8, 31.1 (2C). IR (film): ν=3446, 2964, 2930, 2873, 1832 (C=O), 1724, 1608, 1510, 1463, 1382, 1297, 1249, 1127, 831, 724 cm$^{-1}$. HRMS (ESI): m/z calcd. for $C_{31}H_{36}O_{12}$: 623.2099 [M+Na$^+$]; found: 623.2101. Anal. Calcd. for $C_{31}H_{36}O_{12}$: C 61.99%, H 6.04%, Found: C 61.96%, H 6.06%.

(4Z,4'Z)-4,4'-(5,14-dihydroxy-3,7,12,16-tetraoxaoctadecane-1,18-diylidene)bis(1,3-dioxolan-2-one)

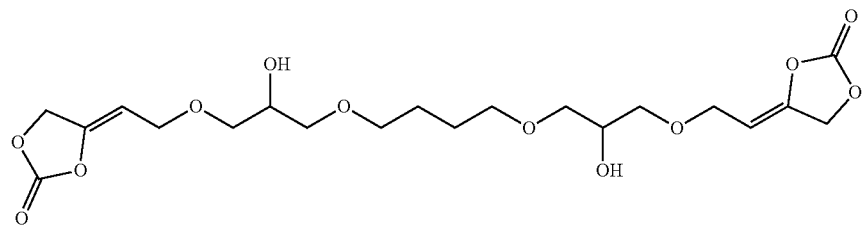 [SMILES: O=C1OC/C(=C/COCC(O)COCCCCOCC(O)COC/C=C2/COC(=O)O2)O1]

Colorless liquid, 426 mg (95%) for a reaction scale of 0.97 mmol. R$_f$ (EtOAc/MeCN 96:4)=0.19. $^1$H NMR (400 MHz, CDCl$_3$): δ=5.03-5.02 (m, 4H), 4.95 (tt, J=7.1 Hz, 2.0 Hz, 2H), 4.20 (t, J=1.4 Hz, 2H), 4.18 (t, J=1.3 Hz, 2H), 3.98-3.91 (m, 2H), 3.55-3.41 (m, 12H), 2.68 (br.s, 1H), 1.67-1.63 (m, 4H). $^{13}$C NMR (100 MHz, CDCl$_3$): δ=152.4 (2C), 144.3 (2C), 100.1 (2C), 71.9 (2C), 71.7 (2C), 71.4 (2C), 69.6 (2C), 67.5 (2C), 64.4 (2C), 26.4 (2C). IR (film): ν=3441, 2919, 2870, 1832 (C=O), 1724, 1465, 1381, 1297, 1214, 1103, 1044, 958, 916, 874, 766, 734, 574 cm$^{-1}$. HRMS (ESI): m/z calcd. for $C_{20}H_{30}O_{12}$: 485.1629 [M+Na$^+$]; found: 485.1627. Anal. Calcd. for $C_{20}H_{30}O_{12}$: C 51.95%, H 6.54%, Found: C 51.97%, H 6.54%.

The invention claimed is:

1. A compound of formula (I),

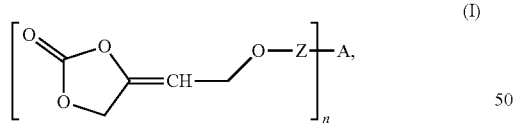

wherein
n is 2, 3 or 4,
Z is a single bond or a divalent organic group which is —CH$_2$—, —C(=O)—, —C(=O)—O—, or —C(=O)—N(R$^5$)—,
A is a polyester, polyurethane, polyether, polyamide, polycarbonate, or a n-valent organic group derived from a C$_1$-C$_{12}$-alkane, saturated C$_3$-C$_{60}$-heterocycle, aromatic C$_6$-C$_{40}$-hydrocarbon, C$_2$-C$_{40}$-heteroarene, or C$_7$-C$_{30}$-arylalkane, wherein, in each member of the n-valent organic group, one or more hydrogen atoms is optionally substituted by halogen, —OH, —NR$^6{}_2$, or —CN and one or more CH$_2$-groups is optionally substituted by —O—, —S—, —N(R$^6$)—, PO$_2$—, —SO$_2$—, —C(=O)—, —C(=O)—O—, or —C(=O)—N(R$^5$)—, R$^5$ being hydrogen, C$_1$-C$_4$ alkyl, or phenyl, and R$^6$ being C$_1$-C$_4$ hydrogen, alkyl, or phenyl.

2. The compound of claim 1, wherein n is 2 or 3.
3. The compound of claim 1, wherein n is 2.
4. The compound of claim 1, wherein R$^5$ is present and is H.
5. A process for preparing the compound of claim 1, the process comprising:
(a) reacting a 4-oxy-but-2-yn-1-ol derivative of formula (II)

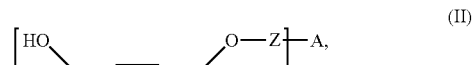

wherein, Z, A, and n, and m have the same meaning as in formula (I),
with carbon dioxide in the presence of at least one transition metal catalyst TMC1 comprising a transition metal of groups 10, 11 of 12 of the IUPAC periodic table of the elements and at least one bulky ligand of formula (III) and/or formula (IV)

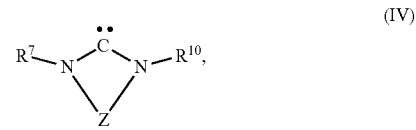

wherein
D is P, As, or Sb,
R$^7$ is an organic radical comprising 1 to 40 carbon atoms,
R$^8$ and R$^9$ are independently an organic radical comprising 1 to 40 carbon atoms,
R$^{10}$ is an organic radical comprising 1 to 40 carbon atoms or is identical to R$^7$, and
Z is —CR$^{12}$=CR$^{13}$—, —CR$^{12}$=N—, —CR$^{12}$R$^{14}$—CR$^{13}$R$^{15}$—, or —CR$^{12}$R$^{14}$—CR$^{13}$R$^{15}$—CR$^{16}$R$^{17}$—, R$^{12}$, R$^{13}$,R$^{14}$,R$^{15}$,R$^{16}$ and R$^{17}$ being independently H, a moiety as defined for R$^{10}$, or two adjacent radicals R$^{12}$ and R$^{13}$ and/or R$^{15}$ and R$^{16}$ together with atoms connecting them form a monocyclic or polycyclic ring system comprising 4 to 40 carbon atoms and optionally Si, Ge, N, P, O, or S.

6. A process for preparing the compound of claim 1, the process comprising:

(b) reacting an alcohol of formula (VI)

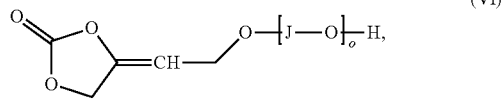

with a compound of formula (VII)

[Q—]$_n$-A (VII), wherein

A, and n, have the same meaning as in formula I,

J is a divalent organic group comprising 1 to 100 carbon atoms,

Q is a functional group capable of reacting with the hydroxy group of the alcohol of formula (VI) in an addition reaction to form an —O-Q(—H)-A unit or Q is a leaving group substituted by the oxygen of the hydroxy group of the alcohol of formula (VI) to form H-Q, and o is 0 or 1.

7. The process of claim 6, wherein Q is —N=C=O, 2-oxiranyl, —C=N—, halide, organic sulfonate, OH, R$^a$C(=O)O, R$^a$O, or imidazole, and wherein R$^a$ is C$_1$-C$_4$ alkyl or phenyl.

8. The process of claim 6, wherein Q is Cl, Br, or I.

9. The process of claim 6, wherein Q is tosylate, mesylate, triflate, or nonaflate.

10. A two-component composition, comprising:

the compound of claim 1, wherein n is 2, 3, 4, 5, or 6, and a multifunctional hardener comprising at least two functional groups which are independently a primary amine, secondary amine, hydroxy group, phosphine, phosphonate, carboxyl group, or mercaptan.

11. A polymer or oligomer, comprising, in reacted form:

the compound of claim 1 used as an intermediate, crosslinker, or monomer.

12. The polymer of claim 11, comprising, in reacted form, the compound as a monomer.

13. The polymer of claim 12, which is a reaction product of the compound of claim 1 and one or more multifunctional compounds comprising at least two functional groups which are independently a primary amine, secondary amine, hydroxy groups, carboxylate, phosphine, phosphonate, or mercaptan.

14. The polymer of claim 13, wherein the multi-functional compound comprises a polyol, polyacid, polyamine, and/or polyamido-amine.

15. A two-component composition, comprising:

the polymer of claim 12; and a multifunctional hardener comprising at least two functional groups which are independently a primary amine, secondary amine, hydroxy group, phosphine, phosphonate, or mercaptan.

16. A component of an adhesive and/or sealant, comprising:

the compound of claim 1, wherein the adhesive and/or sealant is suitable for a rigid and flexible part, made from metal, plastic, paper, paperboard, textile, glass, leather, wood, and/or inorganic material.

17. A coating, comprising:

the compound of claim 1, wherein the coating is suitable for a rigid and flexible substrate, made from metal, plastic, paper, paperboard, textile, glass, leather, wood, and/or inorganic material.

18. A binder suitable for fibers, particles, and/or pigments, the binder comprising the compound of claim 1.

19. A polyunsaturated compound, comprising, in reacted form:

the compound of claim 1, and a (oligo/poly)-functional nucleophile, reacted with the compound of formula (I).

* * * * *